(12) United States Patent
Kurn et al.

(10) Patent No.: US 8,551,709 B2
(45) Date of Patent: Oct. 8, 2013

(54) METHODS FOR FRAGMENTATION AND LABELING OF NUCLEIC ACIDS

(75) Inventors: Nurith Kurn, Palo Alto, CA (US); Pengchin Chen, San Jose, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 0 days.

(21) Appl. No.: 13/411,170

(22) Filed: Mar. 2, 2012

(65) Prior Publication Data

US 2012/0220483 A1   Aug. 30, 2012

Related U.S. Application Data

(63) Continuation of application No. 12/305,633, filed as application No. PCT/US2007/015409 on Jul. 2, 2007, now abandoned.

(60) Provisional application No. 60/817,890, filed on Jun. 30, 2006.

(51) Int. Cl.
 *C12Q 1/68* (2006.01)
 *C12P 19/34* (2006.01)

(52) U.S. Cl.
 USPC ......................................... 435/6.12; 435/91.2

(58) Field of Classification Search
 USPC ............................................. 435/6.12, 91.2
 See application file for complete search history.

(56) References Cited

U.S. PATENT DOCUMENTS

| 5,573,913 | A  | * | 11/1996 | Rosemeyer et al. | .......... 435/6.12 |
| 2003/0119150 | A1 | * | 6/2003 | Ankenbauer et al. | ........ 435/91.2 |
| 2004/0005614 | A1 | * | 1/2004 | Kurn et al. | ........................ 435/6 |
| 2004/0161742 | A1 |   | 8/2004 | Dean et al. | |
| 2005/0059048 | A1 |   | 3/2005 | Gunderson et al. | |
| 2010/0022403 | A1 |   | 1/2010 | Kurn et al. | |
| 2011/0105364 | A1 |   | 5/2011 | Kurn | |
| 2011/0189679 | A1 |   | 8/2011 | Kurn et al. | |
| 2011/0224105 | A1 |   | 9/2011 | Kurn et al. | |

FOREIGN PATENT DOCUMENTS

| EP | 2272976 A1 | 1/2011 |
| WO | WO 2011/003630 A1 | 1/2011 |

OTHER PUBLICATIONS

U.S. Appl. No. 13/156,294, filed Jun. 8, 2011, Raymond et al.
Office action dated Feb. 8, 2012 for EP Application No. 07810169.8.
Office action dated Feb. 17, 2011 for U.S. Appl. No. 12/305,633.
Office action dated Mar. 1, 2010 for U.S. Appl. No. 10/441,663.
Office action dated Mar. 7, 2007 for U.S. Appl. No. 10/441,663.
Office action dated May 16, 2011 for U.S. Appl. No. 11/948,784.
Office action dated May 25, 2006 for U.S. Appl. No. 10/441,663.
Office action dated Jul. 5, 2007 for U.S. Appl. No. 10/441,663.
Office action dated Jul. 8, 2009 for U.S. Appl. No. 10/441,663.
Office action dated Jul. 15, 2007 for U.S. Appl. No. 10/441,663.
Office action dated Aug. 18, 2010 for U.S. Appl. No. 12/305,633.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Dec. 5, 2008 for U.S. Appl. No. 10/441,663.
Office action dated Dec. 17, 2007 for U.S. Appl. No. 10/441,663.
Freeman, et al. Fundamentals of DNA Hybridization Arrays for Gene Expression Analysis. BioTechniques Nov. 29, 2000: 1042-1044, 1048-1055.
Office action dated Jun. 6, 2012 for U.S. Appl. No. 10/441,663.
U.S. Appl. No. 13/643,056, filed Oct. 23, 2012, Armour.
Borodina, et al., A strand-specific library preparation protocol for RNA sequencing. Chpater 5. Methods in Enzymology. Sep. 20, 2011; 500:79-98.
International search report and written opinion dated Feb. 12, 2013 for PCT/US2012/061218.
Levin, et al. Comprehensive comparative analysis of strand-specific RNA sequencing methods. Nat Methods. Sep. 2010;7(9):709-15 doi: 10.1038/meth. 1491, Epub Aug. 15, 2010.
Office action dated Jun. 30, 2008 for U.S. Appl. No. 11/026,280.
Office action dated Jul. 13, 2007 for U.S. Appl. No. 11/026,280.
Office action dated Nov. 13, 2012 for U.S. Appl. No. 12/855,611.
European search report and search opinion dated Apr. 3, 2013 for Application No. 10808789.1.
Office action dated Jun. 19, 2013 for U.S. Appl. No. 12/855,611.
Combined search and examination report dated Apr. 24, 2013 for GB1305340.

* cited by examiner

*Primary Examiner* — Kenneth R. Horlick
*Assistant Examiner* — Joyce Tung
(74) *Attorney, Agent, or Firm* — Wilson, Sonsini, Goodrich & Rosati

(57) ABSTRACT

The invention provides methods, compositions, and kits for fragmentation and labeling of nucleic acids. More particularly, the invention relates to methods for fragmentation of nucleic acids to produce fragments with 3' end hydroxyl groups within a desired size range. In methods of the invention, nucleic acids are fragmented at abasic sites to produce fragments with blocked 3' ends. The 3' ends are unblocked to produce polynucleotide fragments with hydroxyl groups at their 3' ends. Methods, kits, and compositions for carrying out fragmentation of a polynucleotide template in a single reaction mixture to yield fragments with 3'-hydroxyl ends within the desired size range are disclosed.

29 Claims, 3 Drawing Sheets

METHODS FOR FRAGMENTATION AND LABELING OF NUCLEIC ACIDS

CROSS-REFERENCE TO RELATED APPLICATIONS

This application is a continuation of U.S. Utility application Ser. No. 12/305,633, filed Jul. 6, 2009, which is a U.S. national application based on PCT/US2007/15409, filed Jul. 2, 2007, which claims priority to U.S. Provisional Patent Application No. 60/817,890, filed Jun. 30, 2006, each of which is incorporated herein by reference in its entirety.

TECHNICAL FIELD

The invention relates to methods for fragmentation of nucleic acids, in particular to generate fragments with 3' end hydroxyl groups, and methods for labeling the fragments.

BACKGROUND

Nucleic acid fragmentation and labeling has gained importance in the field of nucleic acid analysis. Fragmented and labeled nucleic acids are useful for efficient hybridization based nucleic acid analysis, particularly when hybridizing to immobilized probes, such as in multiplex detection using microarrays or bead based hybridization assays. Fragmentation of nucleic acids to generate fragments having hydroxyl groups at their 3' termini is useful since a 3' hydroxyl group permits extension with a template-dependent polymerase or labeling with a template-independent polymerase, which permits introduction of a label. The extension of fragmented, hybridized nucleic acid along a nucleic acid probe or template molecule by target directed nucleic acid synthesis is useful for both nucleic acid analysis and the generation of recombinant nucleic acids.

A method for controlled nucleic acid fragmentation has been previously described which is based on the incorporation of non-canonical nucleotides into a polynucleotide strand which is synthesized in vitro, followed by generation of an abasic site at the site of incorporation of a non-canonical nucleotide, permitting subsequent fragmentation of the synthesized polynucleotide and/or labeling at the abasic site. (U.S. Patent Application No. 2004/0005614; PCT Application No. WO 04/011665). The size distribution of the fragmented products may be controlled by the level of incorporation of non-canonical nucleotides. The level of incorporation, and subsequent nucleic acid fragment size, may be adjusted to provide a suitable fragment size for the particular downstream use of the fragmented products.

A process utilizing dUTP as the non-canonical nucleotide during DNA synthesis, uracil N-glycosylase ("UNG") as the enzyme which removes the base portions of the non-canonical nucleotides to generate abasic sites, and cleavage of abasic sites with a polyamine, such as N,N'-dimethylethylenediamine, as described in U.S. Application No. 2004/0005614 and PCT Application No. WO 04/011665, results in the generation of fragmented polynucleotides with modified ("blocked") 3' ends that are capable of reacting with an aldehyde-reactive reagent. This process is useful for generation of fragmented and labeled nucleic acids suitable for analysis, for example, on a microarray, or fragmented nucleic acid targets suitable for immobilization.

The process of controlled fragmentation and labeling of single stranded nucleic acids is difficult to achieve using other methods, such as non-specific digestion with an enzyme such as DNase or chemical nucleotide modification, since these reactions cannot be carried out to completion without complete, or nearly complete, degradation of the single stranded nucleic acid to be fragmented and labeled. Double stranded DNA may be digested with restriction endonucleases to generate fragments of defined size distribution. Such enzymes are specific for a defined sequence content, both with respect to composition and length of a recognition site, and afford higher or lower frequency of cleavage depending on the restriction enzyme used. However, restriction endonucleases are specific for double stranded DNA and this approach does not apply to fragmentation of single stranded nucleic acid molecules.

A desirable feature for fragmented nucleic acids is the presence of a hydroxyl group at the 3' end, which may serve as a substrate for polynucleotide synthesis with a polymerase via template-dependent or template-independent extension, or ligation with another polynucleotide. Such manipulations may facilitate introduction of a label. For example, a label may be introduced by extending from the 3' end with terminal transferase (a template-independent polymerase) and a labeled nucleotide. The method described above, in which nucleic acid molecules are cleaved at an abasic site with a polyamine, results in nucleic acids with "blocked" 3' ends, precluding use of the fragments as primers for polynucleotide synthesis or substrates for labeling at a 3' hydroxyl group.

New methods for the efficient fragmentation of nucleic acids to generate fragments comprising 3' end hydroxyl groups, and of defined size distribution, are desirable.

BRIEF SUMMARY OF THE INVENTION

The invention provides methods, compositions, and kits for fragmenting, or fragmenting and labeling, a polynucleotide.

In one aspect, the invention features the generation and/or use of a polynucleotide with abasic sites distributed such that cleavage at the abasic sites generates fragments of a desired size range.

In one aspect, the invention provides a method for fragmenting a polynucleotide, said method comprising: (a) chemically cleaving a phosphodiester backbone of a polynucleotide comprising an abasic site at or near the abasic site, whereby a polynucleotide fragment comprising a blocked 3' end is generated; and (b) contacting the polynucleotide fragment with an enzyme capable of unblocking (i.e., which unblocks) the blocked 3' end of said fragment, whereby a polynucleotide fragment comprising a 3' end hydroxyl group is generated. In some embodiments, steps (a) and (b) are performed simultaneously in the same reaction mixture. In some embodiments, fragments within a desired size range are generated.

In some embodiments, the phosphodiester backbone is cleaved with a polyamine to generate a polynucleotide fragment with a blocked 3' end. In one embodiment, the polyamine is N,N'-dimethylethylenediamine (DMED).

In some embodiments, the enzyme capable of unblocking the blocked 3' end comprises a 3' to 5' exonuclease activity. In one embodiment, the exonuclease activity is a non-processive exonuclease activity. In one embodiment, the enzyme that comprises an exonuclease activity does not comprise an endonuclease activity. In one embodiment, the enzyme that comprises an exonuclease activity also comprises an endonuclease activity, and contacting the polynucleotide fragment with the enzyme is under conditions in which the endonuclease activity is minimized or absent. In one embodiment, the enzyme comprising a 3' exonuclease activity is selected from the group consisting of endonuclease 4, exonuclease T, and apurinic/apyrimidinic endonuclease (APE 1).

In some embodiments, the method further comprises extending the polynucleotide fragment from the 3' hydroxyl group with a template independent polymerase and a labeled nucleotide, whereby a polynucleotide fragment labeled at the 3' end is generated. In one embodiment, the template independent polymerase is terminal deoxynucleotidyl transferase (TdT). In one embodiment, the labeled nucleotide is a biotinylated nucleotide. In various embodiments, the biotinylated nucleotide is selected from the group consisting of a biotinylated nucleotide triphosphate (NTP), a biotinylated deoxynucleotide triphosphate (dNTP), and a biotinylated dideoxynucleotide triphosphate (ddNTP). In some embodiments, the biotinylated nucleotide is selected from the group consisting of biotin 2',3'-dideoxy-UTP and biotin 2',3'-dideoxy-CTP. In one embodiment, the labeled nucleotide comprises a fluorophore. In one embodiment, a mixture of labeled and unlabeled nucleotides is used for labeling the polynucleotide fragment. As used herein, the term "nucleotide" encompasses nucleotide analogs, which are known in the art. The term "labeled nucleotide" encompasses labeled nucleotide analogs.

In some embodiments, the polynucleotide comprising an abasic site is generated by: (i) synthesizing a polynucleotide from a polynucleotide template in the presence of a non-canonical nucleotide, whereby a polynucleotide comprising the non-canonical nucleotide is generated; and (ii) cleaving a base portion of the non-canonical nucleotide from the synthesized polynucleotide with an enzyme capable of cleaving (i.e., which cleaves) the base portion of the non-canonical nucleotide, whereby an abasic site is generated. In some embodiments, the method involves synthesizing the polynucleotide from the polynucleotide template in the presence of all four canonical nucleotides and a non-canonical nucleotide, wherein the non-canonical nucleotide is provided at a ratio suitable for generating fragments within the desired size range. In various embodiments, the non-canonical nucleotide is selected from the group consisting of dUTP, dITP, and 5-OH-Me-dCTP. In one embodiment, the enzyme capable of cleaving a base portion of the non-canonical nucleotide is an N-glycosylase. In some embodiments, the N-glycosylase is selected from the group consisting of Uracil N-Glycosylase (UNG), hypoxanthine-N-Glycosylase, and hydroxy-methyl cytosine-N-glycosylase. In one embodiment, the non-canonical nucleotide is dUTP and the enzyme capable of cleaving a base portion of the non-canonical nucleotide is UNG. In one embodiment, the non-canonical nucleotide is dUTP, the enzyme capable of cleaving a base portion of the non-canonical nucleotide is UNG, and the phosphodiester backbone is cleaved with DMED. In one embodiment, the polynucleotide comprising a non-canonical nucleotide is synthesized using a primer comprising a non-canonical nucleotide. In one embodiment, the polynucleotide comprising a non-canonical nucleotide is synthesized in the presence of two or more different non-canonical nucleotides, whereby a polynucleotide comprising two or more different non-canonical nucleotides is synthesized. In one embodiment, polynucleotides comprising a non-canonical nucleotides are synthesized from two or more different polynucleotide templates. In some embodiments, the polynucleotide comprising an abasic site is generated by non-enzymatically converting a canonical or non-canonical nucleotide in a polynucleotide into an abasic site. Exemplary non-enzymatic methods for generating an abasic site include depurination or depyrimidination of a nucleotide using an acidic pH, an oxidizing agent, an alkylating agent, and any two or more of the foregoing.

In some embodiments, the polynucleotide comprising an abasic site is generated by cleaving a base portion of a methylated nucleotide with an agent capable of cleaving (i.e., which cleaves) a base portion of the methylated nucleotide to create an abasic site, whereby an abasic site is generated. In some embodiments, the method includes cleaving a base portion of a methylated nucleotide in a polynucleotide with an agent capable of cleaving a base portion of the methylated nucleotide to create an abasic site, whereby the polynucleotide comprising an abasic site is generated.

In some embodiments, the polynucleotide comprising an abasic site is generated by cleaving a base portion of a canonical nucleotide with an agent capable of cleaving (i.e., which cleaves) a base portion of the canonical nucleotide to create an abasic site, whereby an abasic site is generated. In some embodiments, the method includes cleaving a base portion of a canonical nucleotide in a polynucleotide with an agent capable of cleaving a base portion of the canonical nucleotide to create an abasic site, whereby the polynucleotide comprising an abasic site is generated. In one embodiment, the canonical nucleotide is cytosine and the agent capable of cleaving a base portion of the canonical nucleotide comprises cytosine deaminase in conjunction with UNG.

In some embodiments, the polynucleotide comprising an abasic site is synthesized from a polynucleotide template comprising DNA or RNA. In various embodiments, the polynucleotide template is selected from the group consisting of RNA, mRNA, cDNA, and genomic DNA. In one embodiment, the polynucleotide comprising an abasic site is single stranded. In one embodiment, the polynucleotide comprising an abasic site is double stranded.

In some embodiments of the methods of the invention, the polynucleotide to be fragmented (i.e., the polynucleotide comprising an abasic site) is synthesized using a method comprising: (a) extending a composite primer in a complex comprising: (i) a polynucleotide template; and (ii) the composite primer, said composite primer comprising an RNA portion and a 3' DNA portion, wherein the polynucleotide template is hybridized to the composite primer; and (b) cleaving RNA of the annealed composite primer with an enzyme that cleaves RNA from an RNA/DNA hybrid such that another composite primer hybridizes to the template and repeats primer extension and strand displacement, whereby multiple copies of the complementary sequence of the polynucleotide template are produced. In one embodiment, the complex of part (a) comprises: (i) a complex of first and second primer extension products, wherein the first primer extension product is produced by extension of a first primer hybridized to a target RNA with at least one enzyme comprising RNA-dependent DNA polymerase activity, wherein the first primer is a composite primer comprising an RNA portion and a 3' DNA portion; wherein RNA in the complex of first and second primer extension products is cleaved with at least one enzyme that cleaves RNA from an RNA/DNA hybrid such that a composite primer hybridizes to the second primer extension product; and (ii) the composite primer.

In some embodiments of the methods of the invention, the polynucleotide to be fragmented (i.e., the polynucleotide comprising an abasic site) is synthesized by an amplification method selected from the group consisting of polymerase chain reaction (PCR), strand displacement amplification (SDA), multiple displacement amplification (MDA), rolling circle amplification (RCA), single primer isothermal amplification (SPIA), and Ribo-SPIA. In some embodiments, the polynucleotide is synthesized by a method selected from the group consisting of reverse transcription, primer extension, limited primer extension, replication, and nick translation. In one embodiment, the polynucleotide is synthesized using a labeled primer.

In one embodiment, the invention provides a method for fragmenting and labeling a polynucleotide, said method comprising: (a) synthesizing a polynucleotide from a polynucleotide template in the presence of a non-canonical nucleotide, whereby a polynucleotide comprising the non-canonical nucleotide is generated; (b) cleaving a base portion of the non-canonical nucleotide from the synthesized polynucleotide with an enzyme capable of cleaving (i.e., which cleaves) the base portion of the non-canonical nucleotide, whereby an abasic site is generated; (c) cleaving the phosphodiester backbone of the polynucleotide comprising the abasic site at or near the abasic site, whereby a polynucleotide fragment comprising a blocked 3' end is generated; (d) contacting the polynucleotide fragment with an enzyme capable of unblocking (i.e., which unblocks) the blocked 3' end of said fragment, whereby a polynucleotide fragment comprising a 3' hydroxyl group is generated; and (e) contacting the polynucleotide fragment comprising a 3' hydroxyl group with an enzyme capable of extending (i.e., which extends) the polynucleotide fragment from the 3' end and a labeled nucleotide, whereby a labeled polynucleotide fragment is generated. In some embodiments, steps (b), (c), and (d) are performed simultaneously. In some embodiments, steps (b), (c), and (d) are performed simultaneously in the same reaction mixture. In some embodiments, steps (b) and (c) are performed simultaneously. In some embodiments, steps (b) and (c) are performed simultaneously in the same reaction mixture. In some embodiments, steps (c) and (d) are performed simultaneously. In some embodiments, steps (c) and (d) are performed simultaneously in the same reaction mixture. In some embodiments, the method involves synthesizing the polynucleotide from the polynucleotide template in the presence of all four canonical nucleotides and a non-canonical nucleotide, wherein the non-canonical nucleotide is provided at a ratio suitable for generating fragments within the desired size range. In some embodiments, labeled fragments within a desired size range are generated.

In one embodiment, the invention provides a method for fragmenting a polynucleotide, said method comprising: (a) incubating a reaction mixture, said reaction mixture comprising: (i) a polynucleotide template; and (ii) a non-canonical nucleotide; wherein the incubation is under conditions that permit synthesis of a polynucleotide comprising the non-canonical nucleotide, whereby a polynucleotide comprising the non-canonical nucleotide is generated; (b) incubating a reaction mixture, said reaction mixture comprising: (i) the polynucleotide comprising the non-canonical nucleotide; and (ii) an enzyme capable of cleaving (i.e., which cleaves) a base portion of the non-canonical nucleotide, wherein the incubation is under conditions that permit cleavage of the base portion of the non-canonical nucleotide, whereby a polynucleotide comprising an abasic site is generated; (c) incubating a reaction mixture, said reaction mixture comprising: (i) the polynucleotide comprising the abasic site; and (ii) an agent capable of chemically cleaving (i.e., which cleaves) the phosphodiester backbone of the polynucleotide comprising the abasic site at or near the abasic site, wherein the incubation is under conditions that permit cleavage of the phosphodiester backbone of the polynucleotide at or near the abasic site, whereby a polynucleotide fragment comprising a blocked 3' end is generated; and (d) incubating a reaction mixture, said reaction mixture comprising: (i) the fragment of the polynucleotide comprising a blocked 3' end; and (ii) an enzyme capable of unblocking (i.e., which unblocks) the blocked 3' end, whereby a polynucleotide fragment comprising a 3' hydroxyl group is generated. In some embodiments, the method further comprises: (e) incubating a reaction mixture, said reaction mixture comprising: (i) the polynucleotide fragment comprising a 3' hydroxyl group; and (ii) an agent capable of extending (i.e., which extends) the fragment from the 3' hydroxyl group; and (iii) a labeled nucleotide, wherein the incubation is under conditions that permit extension of the polynucleotide fragment from the 3' hydroxyl group, whereby a labeled polynucleotide fragment is generated. In one embodiment, the agent capable of extending the polynucleotide fragment from the 3' hydroxyl group is TdT, wherein the polynucleotide fragment is labeled at the 3' hydroxyl group with a labeled nucleotide. In some embodiments, steps (b), (c), and (d) are performed simultaneously in the same reaction mixture. In some embodiments, the incubation is under conditions that permit synthesis of the polynucleotide from the polynucleotide template in the presence of all four canonical nucleotides and a non-canonical nucleotide, wherein the non-canonical nucleotide is provided at a ratio suitable for generating fragments within the desired size range. In some embodiments, fragments within a desired size range are generated.

In one embodiment, the invention provides a method for generating a polynucleotide fragment with a 3' end hydroxyl group, comprising contacting a polynucleotide fragment with a blocked 3' end with an enzyme capable of unblocking (i.e., which unblocks) the blocked 3' end, wherein the polynucleotide fragment with a blocked 3' end is generated by cleaving a polynucleotide fragment comprising an abasic site at or near the abasic site.

In another aspect, the invention provides, a method of characterizing a polynucleotide template of interest, comprising analyzing a labeled polynucleotide fragment produced by a method as described herein. In one embodiment, the method comprises (a) generating a labeled polynucleotide fragment by a method as described herein; and (b) analyzing the labeled polynucleotide fragment. In one embodiment, analyzing the labeled polynucleotide fragment comprises determining amount of said products, whereby the amount of the polynucleotide template present in a sample is quantified. In one embodiment, analyzing the labeled polynucleotide fragment comprises contacting the labeled polynucleotide fragment with at least one probe. In one embodiment, the at least one probe is provided as a microarray. In one embodiment, the microarray is a high density polynucleotide microarray. In one embodiment, the microarray is a high density oligonucleotide microarray. In some embodiments, the microarray comprises at least one probe immobilized on a substrate fabricated from a material selected from the group consisting of paper, glass, ceramic, plastic, polypropylene, polystyrene, nylon, polyacrylamide, nitrocellulose, silicon, and optical fiber. In one embodiment, the at least one probe is immobilized on the substrate in a two-dimensional configuration or a three-dimensional configuration comprising pins, rods, fibers, tapes, threads, beads, particles, microtiter wells, capillaries, and cylinders.

In another aspect, the invention provides a method of determining gene expression profile in a sample, said method comprising determining the amount of labeled polynucleotide fragment from at least one polynucleotide fragment produced by a method as described herein, wherein the amount is indicative of amount of a polynucleotide template from which the polynucleotide fragment was generated in a sample, whereby a gene expression profile is determined. In one embodiment, the method comprises (a) generating a labeled polynucleotide fragment from at least one polynucleotide template in the sample using a method as described herein; and (b) determining amount of labeled polynucleotide fragment from a polynucleotide template, wherein said amount is indicative of amount of the polynucleotide template in the sample, whereby the a gene expression profile in the sample is determined. In one embodiment, the polynucleotide template is RNA or mRNA. In one embodiment, the amounts of a plurality of polynucleotide fragments derived from a plurality of polynucleotide templates in a sample is determined.

In another aspect, the invention provides a method of generating hybridization probes, comprising generating a labeled polynucleotide fragment using a method as described herein.

In another aspect, the invention provides a method for nucleic acid hybridization, comprising hybridizing a labeled polynucleotide fragment with at least one probe, wherein the labeled polynucleotide fragment is generated using a method as described herein. In one embodiment, the method comprises (a) generating a labeled polynucleotide fragment using a method as described herein; and (b) hybridizing the labeled polynucleotide fragment with at least one probe.

In another aspect, the invention provides a method for comparative hybridization, comprising comparing hybridization of a first population of labeled polynucleotide fragments prepared using a method as described herein to at least one probe with hybridization of a second population of labeled polynucleotide to the at least one probe. In one embodiment, the method comprises (a) preparing a first population of labeled polynucleotides fragments from a first template polynucleotide sample using a method as described herein; and (b) comparing hybridization of the first population to at least one probe with hybridization of a second population of labeled polynucleotide. In one embodiment, the first population and second population comprise detectably different labels. In one embodiment, the second population of labeled polynucleotides are prepared from a second polynucleotide sample using a method as described herein. In one embodiment, comparing comprises determining amount of said products, whereby the amount of the first and second polynucleotide templates is quantified. In one embodiment, the first and/or second template polynucleotides from which the first and/or second populations of labeled polynucleotides are prepared comprise genomic DNA.

In another aspect, the invention provides a method for detecting presence or absence of a mutation in a template, comprising analyzing a labeled polynucleotide fragment prepared by a method as described herein, whereby presence of absence of a mutation is detected. In one embodiment, the method comprises (a) generating a labeled polynucleotide fragment by a method as described herein; and (b) analyzing the labeled polynucleotide fragment, whereby presence or absence of a mutation is detected. In one embodiment, the labeled polynucleotide fragment is compared to a reference template. In various embodiments, the mutation is selected from the group consisting of a base substitution, a base insertion, a base deletion, and a single nucleotide polymorphism.

In another aspect, the invention provides a composition comprising: (a) an agent capable of cleaving (i.e., which cleaves) a base portion of a nucleotide to generate an abasic site in a polynucleotide; (b) an agent capable of cleaving (i.e., which cleaves) a phosphodiester backbone at or near an abasic site to produce a polynucleotide fragment with a blocked 3' end; and (c) an enzyme capable of unblocking (i.e., which unblocks) a blocked 3' end to generate a polynucleotide comprising a 3' hydroxyl group. In one embodiment, (a) is an N-glycosylase, (b) is a polyamine, and (c) is an enzyme comprising a 3' exonuclease activity. In one embodiment, (a) is UNG, (b) is DMED, and (c) is selected from the group consisting of endonuclease 4, exonuclease T, and APE 1.

In another aspect, the invention provides a kit comprising: (a) an agent capable of cleaving (i.e., which cleaves) a base portion of a nucleotide to generate an abasic site in a polynucleotide; (b) an agent capable of cleaving (i.e., which cleaves) a phosphodiester backbone at or near an abasic site to produce a polynucleotide fragment with a blocked 3' end; and (c) an enzyme capable of unblocking (i.e., which unblocks) a blocked 3' end to generate a polynucleotide comprising a 3' hydroxyl group. In one embodiment, the kit further comprises: (d) an agent capable of labeling (i.e., which labels) a 3' hydroxyl group of a polynucleotide. In one embodiment, (a) is an N-glycosylase, (b) is a polyamine, (c) is an enzyme comprising a 3' exonuclease activity; and (d) is a template independent polymerase. In one embodiment, (a) is UNG, (b) is DMED, (c) is selected from the group consisting of endonuclease 4, exonuclease T, and APE 1; and (d) is TdT. In some embodiments, the kit further comprises a non-canonical nucleotide. In some embodiments, the kit further comprises a non-canonical nucleotide and an enzyme capable of synthesizing a polynucleotide comprising the non-canonical nucleotide. In one embodiment, the non-canonical nucleotide is dUTP and the agent capable of cleaving a base portion of a nucleotide to generate an abasic site in a polynucleotide is UNG.

In some embodiments, the kit further comprises: (e) a labeled nucleotide. In one embodiment, (a) is an N-glycosylase, (b) is a polyamine, (c) is an enzyme comprising a 3' exonuclease activity; (d) is a template independent polymerase; and (e) is a biotinylated nucleotide. In some embodiments, (e) is selected from the group consisting of a biotinylated nucleotide triphosphate (NTP), a biotinylated deoxynucleotide triphosphate (dNTP), and a biotinylated dideoxynucleotide triphosphate (ddNTP). In one embodiment, (a) is UNG, (b) is DMED, (c) is selected from the group consisting of endonuclease 4, exonuclease T, and APE 1; (d) is TdT, and (e) is selected from the group consisting of biotin 2',3'-dideoxy-UTP and biotin 2',3'-dideoxy-CTP.

In some embodiments, a kit of the invention comprises, in addition to the components described above, a template dependent DNA polymerase; a composite primer, wherein the composite primer comprises a 5' RNA portion and a 3' DNA portion; and an agent capable of cleaving RNA from an RNA-DNA hybrid. In some embodiments, the RNA portion of the composite primer is 5' with respect to the 3' DNA portion, the 5' RNA portion is adjacent to the 3' DNA portion, the RNA portion of the composite primer consists of about 5 to about 50 nucleotides and the DNA portion of the composite primer consists of 1 to about 20 nucleotides. In one embodiment, the agent that cleaves RNA from an RNA-DNA hybrid is RNAse H.

Kits of the invention generally comprise packaging, and may comprise instructions for use in a method for polynucleotide fragmentation, or polynucleotide fragmentation and labeling, as described herein.

DETAILED DESCRIPTION

Figure 1:
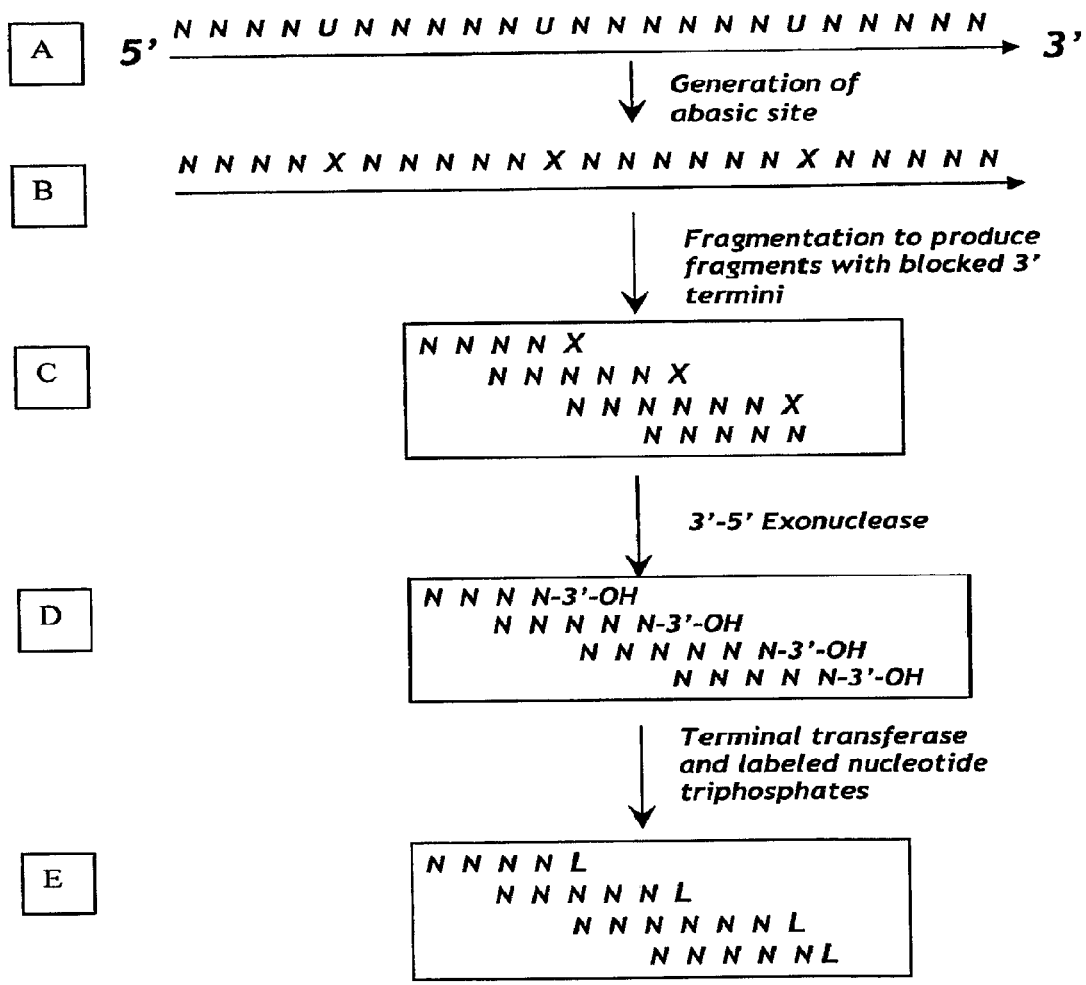
FIG. 1 schematically depicts an embodiment of a nucleic acid fragmentation and labeling procedure as described herein. A single stranded nucleic acid comprising non-canonical nucleotide dU (A) is used to generate a nucleic acid with abasic sites (B). Non-canonical nucleotides are denoted as "U" in nucleic acid A and canonical nucleotides are denoted as "N." Abasic sites are denoted as "X" in nucleic acid B. The nucleic acid is fragmented at the abasic sites to generate fragments with blocked 3' termini (C). A 3'-5' exonuclease is used to unblock the 3' termini of fragments C, thereby generating nucleic acid fragments with 3' hydroxyl groups (D). The 3' hydroxyl groups serve as substrates for end labeling using terminal transferase and labeled nucleotide triphosphates, thereby producing labeled nucleic acid fragments (E). The end labels are denoted as "L" in fragments E.

Methods for Generating Fragmented Polynucleotides with 3' End Hydroxyl Groups

The invention provides novel methods, compositions, and kits for fragmenting polynucleotides to generated polynucleotide fragments with hydroxyl groups at their 3' ends. The methods, compositions, and kits of the invention are useful for fragmenting and labeling polynucleotides. These methods are suitable for, for example, generation of labeled polynucleotide fragments, for use as hybridization probes, or generation of polynucleotide fragments which may be hybridized to a polynucleotide template and extended with a template dependent polymerase.

In methods of the invention, a polynucleotide is cleaved at or near an abasic site present in the polynucleotide. The abasic site may be prepared by cleavage of a base portion of a non-canonical nucleotide present in the polynucleotide, cleavage of a base portion of a canonical nucleotide present in the polynucleotide, or cleavage of a base portion of a methylated nucleotide present in the polynucleotide. For methods in which an abasic site is generated by cleavage of a base portion of a non-canonical nucleotide, the spacing of non-canonical nucleotides in the polynucleotide to be fragmented and labeled, relates to and determines the size of fragments and intensity of labeling. This feature permits control of fragment size and/or site of labeling by use of conditions permitting controlled incorporation of non-canonical nucleotide, for example, during synthesis of the polynucleotide comprising the non-canonical nucleotide from a polynucleotide template.

Cleavage at or near an abasic site is generally effected with an agent or under conditions which do not generate a 3' hydroxyl group, i.e., conditions that generate a "blocked" 3' end that contains a non-nucleotide moiety, such as an aldehyde group (e.g., the sugar residue remaining behind after generation of the abasic site), at the 3' end.

Generally, a chemical fragmentation method is used, wherein a polynucleotide fragment comprising a blocked 3' end is generated. In some embodiments, chemical fragmentation at or near an abasic site is effected with a polyamine, such as, for example, N,N'-dimethylethylenediamine (DMED), which produces polynucleotide fragments with blocked 3' ends. Cleavage with a polyamine most commonly employs a β- or β-γ elimination mechanism. β-elimination results in cleavage of the 3'-phosphodiester bond and a remnant of the sugar moiety (an aldehyde) is attached to the 3' end. Depending on the cleavage agent used, other modifications of the 3' end are also possible, such as a 3'-phosphoglycolate group. Blocked 3' ends may be unblocked by digestion with an enzyme capable of removing the attached blocking moiety, such as a 3' to 5' exonuclease, preferably a non-processive exonuclease, thereby producing polynucleotide fragments with a 3' end hydroxyl group. In some embodiments, an enzyme that comprises an exonuclease activity and does not comprise endonuclease activity is used. In some embodiments, an enzyme that comprises both exonuclease and endonuclease activities is used. In one embodiment, an enzyme that comprises both exonuclease and endonuclease activities is used under conditions in which the endonuclease activity is substantially minimized or absent. In some embodiments, endonuclease 4, exonuclease T, or the 3' to 5' exonuclease activity of the apurinic/apyrimidinic endonuclease (APE 1) is used.

In some embodiments, polynucleotide fragments with unblocked 3' ends are labeled with an agent capable of labeling at 3' hydroxyl groups of polynucleotides. In some embodiments, a template independent polymerase is used for labeling. In one embodiment, the template independent polymerase is terminal deoxynucleotidyl transferase (TdT), an enzyme which is capable of attaching one or more nucleotides (i.e., labeled nucleotides, unlabeled nucleotides, or a mixture of labeled and unlabeled nucleotides) at a polynucleotide 3' end hydroxyl group by extension of the polynucleotide from the 3' end. "Labeled" or "detectable" nucleotide or polynucleotide, as used herein, refers to a nucleotide (or nucleotide analog thereof) or polynucleotide that is directly or indirectly detectable. A nucleotide may comprise a directly-detectable label such as, for example, a fluorophore (e.g., cy dyes, alexa dyes, fluorescein, etc.), an enzyme, a chromophore, or a radiolabel, or the nucleotide may comprise an indirectly-detectable label such as a hapten which is detectable by binding of a labeled second member of a specific binding pair, such as, for example, biotin/avidin or streptavidin, antigen/antibody, etc., and the label attached to the second member of the binding pair may be, for example, a fluorophore, an enzyme, a chromophore, or a radiolabel, or the second member of the binding pair may be attached to a detectable particle. In one embodiment, the nucleotide is a biotinylated nucleotide, such as, for example, biotin 2',3'-dideoxy-UTP, and is detectable by binding of labeled avidin or streptavidin.

In some embodiments, a polynucleotide fragment with an unblocked 3' end, produced as described herein, is hybridized to a polynucleotide template and extended from the 3' hydroxyl group with a template-dependent polymerase, using labeled or unlabeled nucleotides, or a mixture of labeled or unlabeled nucleotides. When labeled polynucleotides are incorporated, a labeled polynucleotide extension product is produced.

In some embodiments, a polynucleotide fragment with an unblocked 3' end, produced as described herein, is ligated to another polynucleotide with a ligase enzyme. If the polynucleotide to which the polynucleotide fragment is ligated is labeled, a labeled ligation product is produced.

In some embodiments, a polynucleotide fragment with an unblocked 3' end, produced as described herein, is "tailed" using a template-independent polymerase, wherein a "tail" of nucleotides, i.e., labeled or unlabeled nucleotides or a mixture thereof, is added at the 3' end of the fragment.

Generation of Abasic Sites in Polynucleotides Comprising Non-Canonical Nucleotides In one aspect, the invention provides methods for fragmenting and labeling a polynucleotide comprising an abasic site produced by incorporation of a non-canonical nucleotide. The methods generally comprise generation of a polynucleotide comprising a non-canonical nucleotide, cleavage of a base portion of the non-canonical nucleotide present in the polynucleotide with an agent (such as an enzyme) capable of cleaving a base portion of the non-canonical nucleotide (whereby an abasic site is generated); chemical cleavage of the phosphodiester backbone at or near the abasic site with an agent or under conditions that do not generate a 3' hydroxyl group, i.e., conditions that generate a polynucleotide fragment having a blocked 3' end; digestion of fragments with an enzyme capable of generating a 3' end with a 3' hydroxyl group from a blocked 3' end; and optionally labeling at the 3' hydroxyl group with an enzyme or agent capable of attaching a label to the 3' hydroxyl group, whereby labeled polynucleotide fragments are generated.

The methods of fragmenting and labeling a polynucleotide generally comprise synthesis of a polynucleotide comprising a non-canonical nucleotide from a polynucleotide template in the presence of a non-canonical nucleotide, whereby a polynucleotide comprising a non-canonical nucleotide(s) is generated.

Non-canonical nucleotides are known in the art and any suitable non-canonical nucleotide can be used. In some embodiments, two or more different non-canonical nucleotides are used, such that a polynucleotide comprising two or more non-canonical nucleotides is generated. Methods for synthesizing polynucleotides from a polynucleotide template are known in the art and described herein, and any suitable method can be used in the methods of the invention. In some embodiments, synthesis of the polynucleotide comprising the non-canonical nucleotides comprises SPIA™ (single primer isothermal amplification; see Kurn, U.S. Pat. Nos. 6,251,639 and 6,692,918), Ribo-SPIA™ (see Kurn, U.S. Pat. No. 6,946,251), PCR, primer extension, reverse transcription, strand displacement amplification (SDA), multiple displacement amplification (MDA), rolling circle amplification (RCA), nick translation based DNA synthesis, DNA replication, and the like. The polynucleotide that is synthesized can be single stranded, double-stranded or partially double stranded, and either or both strands can comprise a non-canonical nucleotide. In some embodiments, the polynucleotide that is synthesized comprises a cDNA. The polynucleotide template (from which the polynucleotide comprising a non-canonical nucleotide is synthesized) is any template from which one desires to produce polynucleotide fragments or labeled fragments thereof. In some embodiments, the template comprises RNA, mRNA, genomic DNA, cDNA, or synthetic DNA. In other embodiments, the template comprises a cDNA library, a subtractive hybridization library, or a genomic library. In one embodiment, the polynucleotide comprising the non-canonical nucleotide is synthesized using limited and/or controlled incorporation of the non-canonical nucleotide, which results in generation of a polynucleotide with a frequency or proportion of non-canonical nucleotides such that, labeled fragments of a desired size (or size range) are generated (following production of an abasic site, cleavage of the phosphodiester backbone at or near an abasic site with an agent or under conditions in which a 3' end comprising a hydroxyl group is not produced (i.e., production of a fragments with blocked hydroxyl groups), generation of hydroxyl groups at the 3' ends on the polynucleotide fragments (i.e., by unblocking the blocked 3' ends, for example, with an enzyme comprising a 3' to 5' exonuclease activity), and labeling of the polynucleotide fragments using polymerase extension from the 3' hydroxyl groups in the presence of a detectable nucleotide or ligation to a detectable polynucleotide (e.g., extension at the 3' hydroxyl groups with a template independent polymerase such as terminal transferase to incorporate one or more detectable nucleotides at the 3' ends).

In some embodiments, a labeled primer is used during synthesis of the polynucleotide comprising a non-canonical nucleotide. In other embodiments, a primer comprising a non-canonical nucleotide (such as dUTP) is used during synthesis of the polynucleotide comprising a non-canonical nucleotide. In other embodiments, the primer is a composite primer, said composite primer comprising a RNA portion and a 3' DNA portion.

It is understood that a polynucleotide comprising a non-canonical nucleotide can be a multiplicity (from small to very large) of different polynucleotide molecules. Such populations can be related in sequence (e.g., members of a gene family or superfamily) or extremely diverse in sequence (e.g., generated from all mRNA, generated from all genomic DNA, etc.). Polynucleotides can also correspond to single sequences (which can be part or all of a known gene, for example, a coding region, genomic portion, etc.).

A base portion of the non-canonical nucleotide is cleaved by an agent (such as an enzyme) capable of cleaving a base portion of a non-canonical nucleotide. Such agents are known in the art and described herein. In one embodiment, the agent capable of specifically cleaving a base portion of a non-canonical nucleotide is an N-glycosylase. In another embodiment, the agent is Uracil N-Glycosylase (interchangeably termed "UNG" or "uracil DNA glyosylase").

Generation of Abasic Sites in Polynucleotides Comprising Methylated Nucleotides

In one aspect, the invention provides methods for fragmenting and labeling a polynucleotide comprising an abasic site produced by cleaving a base portion of a methylated nucleotide with an agent capable of cleaving a base portion of the methylated nucleotide to create an abasic site, whereby an abasic site is generate. The methods generally comprise cleavage of a base portion of a methylated nucleotide with an agent (such as an enzyme) capable of cleaving a base portion of a methylated nucleotide (whereby an abasic site is generated); chemical cleavage of the phosphodiester backbone at or near the abasic site with an agent or under conditions that do not generate a 3' hydroxyl group, i.e., conditions that generate a polynucleotide fragment with a blocked 3' end; digestion of fragments with an enzyme capable of generating a polynucleotide containing a hydroxyl group at the 3' end; and optionally labeling at the 3' end with an enzyme or agent capable of attaching a label to the 3' hydroxyl group, whereby labeled polynucleotide fragments are generated (3' end labeling).

Generation of Abasic Sites in Polynucleotides by Cleaving Base Portions of Canonical Nucleotides In one aspect, the invention provides methods for fragmenting and labeling a polynucleotide comprising an abasic site produced by cleaving a base portion of a canonical nucleotide with an agent capable of cleaving a base portion of the canonical nucleotide to create an abasic site, whereby an abasic site is generated. The methods generally comprise cleavage of a base portion of a canonical nucleotide with an agent (such as an enzyme) capable of cleaving a base portion of a methylated nucleotide (whereby an abasic site is generated); chemical cleavage of the phosphodiester backbone at or near the abasic site with an agent or under conditions that do not generate a 3' hydroxyl group, i.e., conditions that generate a polynucleotide fragment with a blocked 3' end; digestion of fragments with an enzyme capable of generating a polynucleotide containing a hydroxyl group at the 3' end; and optionally labeling at the 3' hydroxyl group with an enzyme or agent capable of attaching a label to the 3' hydroxyl group, whereby labeled polynucleotide fragments are generated.

Fragmentation at Abasic Sites to Produce Polynucleotide Fragments with Blocked 3' Ends In methods of the invention, the phosphodiester backbone of a polynucleotide comprising an abasic site is cleaved at or near the abasic site by an agent capable of cleaving the phosphodiester backbone at or near an abasic site, such that two or more fragments are produced. As used herein, "cleaving the backbone or phosphodiester backbone" is also termed "fragmentation" or "fragmenting." Fragmentation of the polynucleotide comprising an abasic site is conducted with an agent or under conditions in which polynucleotides comprising hydroxyl groups at their 3' ends are substantially not produced. Generally, a chemical fragmentation agent is used, producing polynucleotide fragments with blocked 3' ends. In some embodiments, a polyamine, such as DMED, is used for fragmentation.

Generally, cleavage occurs 3' to the abasic site (e.g., cleavage between the deoxyribose ring and 3'-phosphate group of the abasic residue and the deoxyribose ring of the adjacent nucleotide, generating a free 5' phosphate group on the deoxyribose ring of the adjacent nucleotide), such that an abasic site is located at the 3' end of the resulting fragment. In still other embodiments, more complex forms of cleavage are possible, for example, cleavage such that cleavage of the phosphodiester backbone and cleavage of a portion of the abasic nucleotide results. Selection of reaction conditions also permits control of the degree, level or completeness of the fragmentation reactions. In some embodiments, reaction conditions can be selected such that the cleavage reaction is performed in the presence of a large excess of reagents and allowed to run to completion with minimal concern about excessive cleavage of the polynucleotide (i.e., while retaining a desired fragment size, which may be determined by spacing of the incorporated non-canonical nucleotide, during the synthesis step, above). In other embodiments, reaction conditions are selected such that fragmentation is not complete (in the sense that the backbone at some abasic sites remains uncleaved (unfragmented), such that polynucleotide fragments comprising more than one abasic site are generated. Such fragments comprise internal (unfragmented) abasic sites.

Unblocking of Blocked 3' Ends

The polynucleotide fragments generated by cleavage of the phosphodiester backbone are contacted with an agent, such as an enzyme comprising an exonuclease activity, that is capable of generating a polynucleotide comprising a hydroxyl group at the 3' end from a polynucleotide comprising a blocked 3' end. Preferably, a non-processive exonuclease is used, such as, for example, APE 1. The resulting polynucleotide fragments have unblocked 3' ends, i.e., comprising a hydroxyl group at the 3' end.

In some embodiments, a polynucleotide fragment comprising a 3' end hydroxyl group, produced as described herein, is extended with a template independent or template dependent polymerase. In one embodiment, the polynucleotide fragment may be extended with a template independent polymerase, such as a terminal transferase, to incorporate one or more labeled nucleotide residue (or nucleotide analogs thereof), one or more unlabeled nucleotide residue (or nucleotide analogs thereof) or a mixture of labeled and unlabeled nucleotide residues (or nucleotide analogs thereof), at the 3' end. In another embodiment, the polynucleotide fragment is hybridized to a polynucleotide template and extended by a template dependent polymerase. In another embodiment, the polynucleotide fragment is ligated to another polynucleotide with an enzyme comprising a ligase enzyme.

Labeling of Polynucleotide Fragments at 3' Hydroxyl Groups

Agents capable of labeling at a 3' hydroxyl group of a polynucleotide are known in the art. For example, a template independent polymerase, such as TdT, can be used to attach one or more labeled nucleotides at the 3' hydroxyl group (i.e., extend from the 3' end). In some embodiments, the detectable moiety (label) is directly or indirectly detectable. In some embodiments, the detectable signal is amplified. In some embodiments, the detectable moiety comprises an organic molecule. In other embodiments, the detectable moiety comprises an antibody. In other embodiments, the detectable signal is fluorescent. In other embodiments, the detectable signal is enzymatically generated. In one embodiment, the fragments are labeled by template independent extension with TdT, using a labeled nucleotide triphosphate (or labeled nucleotide analog thereof). In one embodiment, the labeled nucleotide is a biotinylated nucleotide, such as, for example, biotin 2',3'-dideoxy-UTP, biotin-dUTP, or biotin-UTP. Other labeled nucleotides, e.g., dNTPs or NTPs, or terminator nucleotides such as 2',3'-dideoxy-NTPs), or combinations thereof, as well as combinations of labeled and unlabeled nucleotides or dideoxy-nucleotides, may also be used.

The methods of the invention include methods of using polynucleotide fragments and labeled polynucleotides produced by the methods of the invention (so-called "applications"). The invention provides methods to characterize (for example, detect presence or absence of and/or quantify) a sequence of interest by analyzing fragmented and labeled products by detection/quantification methods such as those based on array technologies or solution phase technologies. In some embodiments, the invention provides methods of detecting the presence or absence of mutations.

In other embodiments, the invention provides methods of producing a hybridization probe; hybridization using the hybridization probes; detection using the hybridization probes; characterizing and/or quantitating nucleic acid; preparing a subtractive hybridization probe; comparative genomic hybridization; and determining a gene expression profile, using the fragmented nucleic acids generated by the methods of the invention.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

Definitions

A "template sequence," or "template nucleic acid" or "template" as used herein, is a polynucleotide comprising a sequence of interest, for which synthesis of a complement comprising a non-canonical nucleotide is desired. The template sequence may be known or not known, in terms of its actual sequence. In some instances, the terms "target," "template," and variations thereof, are used interchangeably.

"Polynucleotide," or "nucleic acid," as used interchangeably herein, refer to polymers of nucleotides of any length, and include DNA. The nucleotides can be deoxyribonucleotides, modified nucleotides or bases, and/or their analogs, or any substrate that can be incorporated into a polymer by DNA polymerase. Nucleotides include canonical and non-canonical nucleotides and a polynucleotide can comprise canonical and non-canonical nucleotides. A polynucleotide may comprise modified (altered) nucleotides, such as, for example, modification to the nucleotide structure and or modification to the phosphodiester backbone. As discussed herein modified nucleotide can be canonical nucleotide or non-canonical (cleavable) nucleotides. It is understood, however, that modified nucleotides that are not non-canonical (cleavable) nucleotide under the reaction conditions used in the methods of the invention, if present, generally should not affect the ability of the polynucleotide to undergo cleavage of a base portion of non-canonical nucleotide, such that an abasic site is generated, and/or cleavage of a phosphodiester backbone at an abasic site, such that fragments are generated, and/or immobilization of a polynucleotide (or fragment thereof) to a substrate, as described herein. If present, modification to the nucleotide structure, such as methylated nucleotides may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). It is understood that internucleotide modifications may, e.g., alter the efficiency and/or kinetics of cleavage of the phosphodiester backbone (as when, for example a phosphodiester backbone is cleaved at an abasic site, as described herein). Further, any of the hydroxyl groups ordinarily present in the sugars may be replaced, for example, by phosphonate groups, phosphate groups, protected by standard protecting groups, or activated to prepare additional linkages to additional nucleotides. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including DNA. It is understood, however, that modified nucleotides and/or internucleotide linkages and/or, if present, generally should not affect the ability of the polynucleotide to undergo cleavage of a base portion of a non-canonical nucleotide, such that an abasic site is generated, and/or the ability of a polynucleotide to undergo cleavage of a phosphodiester backbone at an abasic site, such that fragments are generated, and/or the ability of a polynucleotide to be immobilized at an abasic site (such as an abasic site at an end of a polynucleotide and/or an abasic site that is not at an end of a polynucleotide) to a surface, as described herein.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "primer," as used herein, refers to a nucleotide sequence (a polynucleotide), generally with a free 3'-OH group, that hybridizes with a template sequence (such as a template RNA, or a primer extension product) and is capable of promoting polymerization of a polynucleotide complementary to the template. A "primer" can be, for example, an oligonucleotide. It can also be, for example, a sequence of the template (such as a primer extension product or a fragment of an RNA template created following RNase cleavage of a template RNA-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final polynucleotide fragments, labeled polynucleotide, labeled polynucleotide fragments, and/or immobilized polynucleotide or fragment thereof.

A "fragment" of a polynucleotide or oligonucleotide is a contiguous sequence of 2 or more bases. In other embodiments, a fragment (also termed "region" or "portion") is any of about 3, about 5, about 10, about 15, about 20, about 25, about 30 about 35 about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In some embodiments, the fragments can be at least about 3, about 5, about 10, about 15, about 20, about 25, about 30 about 35 about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In other embodiments, the fragments can be less than about 3, about 5, about 10, about 15, about 20, about 25, about 30 about 35 about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In some embodiment, these fragment lengths represent an average size in the population of fragments generated using the methods of the invention.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments. "A" non-canonical nucleotide means one or more non-canonical nucleotides.

Conditions that "allow" or "permit" an event to occur or conditions that are "suitable" for an event to occur, such as polynucleotide synthesis, cleavage of a base portion of a non-canonical nucleotide, cleavage of a phosphodiester backbone at an abasic site, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the polynucleotide sequence, temperature, and buffer conditions. These conditions also depend on what event is desired, such as polynucleotide synthesis, cleavage of a base portion of a non-canonical nucleotide, cleavage of a phosphodiester backbone at an abasic site, labeling an abasic site, immobilizing a polynucleotide fragment or a polynucleotide, etc.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon, polystyrene), polyacrylamide, nitrocellulose, silicon and other metals, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767-773; Pease et al., *Proc. Natl. Acad. Sci. U.S.A.* (1994), 91:5022-5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467-470, DeRisi et al, *Nature Genetics* (1996), 14:457-460; Shalon et al., *Genome Res.* (1996), 6:639-645; and Schena et al., *Proc. Natl. Acad. Sci. U.S.A.* (1995), 93:10539-11286); (iii) by masking (Maskos and Southern, *Nuc. Acids. Res.* (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides.

As used herein, "canonical" nucleotide means a nucleotide comprising one the four common nucleic acid bases adenine, cytosine, guanine and thymine that are commonly found in DNA. The term also encompasses the respective deoxyribonucleosides, deoxyribonucleotides or 2'-deoxyribonucleoside-5'-triphosphates that contain one of the four common nucleic acid bases adenine, cytosine, guanine and thymine (though as explained herein, the base can be a modified and/or altered base as discussed, for example, in the definition of polynucleotide). As used herein, the base portions of canonical nucleotides are generally not cleavable under the conditions used in the methods of the invention.

As used herein, "non-canonical nucleotide" (interchangeably called "non-canonical deoxyribonucleoside triphosphate") refers to a nucleotide comprising a base other than the four canonical bases. The term also encompasses the respective deoxyribonucleosides, deoxyribonucleotides or 2'-deoxyribonucleoside-5'-triphosphates that contain a base other than the four canonical bases. In the context of this invention, nucleotides containing uracil (such as dUTP), or the respective deoxyribonucleosides, deoxyribonucleotides or 2'-deoxyribonucleoside-5'-triphosphates, are a non-canonical nucleotides. As used herein, the base portions of non-canonical nucleotides are capable of being, generally, specifically or selectively cleaved (such that a nucleotide comprising an abasic site is created) under the reaction conditions used in the methods of the invention. As described herein, non-canonical nucleotides are generally also capable of being incorporated into a polynucleotide during synthesis of a polynucleotide (during e.g., primer extension and/or replication); capable of being generally, specifically or selectively cleaved by an agent that cleaves a base portion of a nucleotide, such that a polynucleotide comprising an abasic site is generated; comprise a suitable internucleotide connection (when incorporated into a polynucleotide) such that a phosphodiester backbone at an abasic site (i.e., the non-canonical nucleotide following cleavage of a base portion) is capable of being cleaved by an agent capable of such cleavage; capable of being labeled (following generation of an abasic site); and/or capable of immobilization to a surface (following generation of an abasic site), according to the methods described herein. It is understood that the non-canonical nucleotide may, but does not necessarily, require all of the features described above, depending on the particular method of the invention in which the non-canonical nucleotide is to be used. In some embodiments, non-canonical nucleotides are altered and/or modified nucleotides as described herein. Non-canonical nucleotide refers to a nucleotide that is incorporated into a polynucleotide as well as to a single nucleotide.

The term "analyte" as used herein refers to a substance to be detected or assayed by the method of the present invention, for example, a compound whose properties, location, quantity and/or identity is desired to be characterized. Typical analytes may include, but are not limited to proteins, peptides, nucleic acid segments, cells, microorganisms and fragments and products thereof, organic molecules, inorganic molecules, or any substance for which immobilization sites for binding partner(s) can be developed. As this disclosure clearly conveys, an analyte is a substrate.

As used herein, an "abasic site" refers to the site of incorporation of the non-canonical nucleotide following treatment with an agent capable of effecting cleavage of a base portion of the non-canonical nucleotide. An abasic site (interchangeably termed "AP site") can comprise a hemiacetal ring, and lacks a base portion of the non-canonical nucleotide. As used herein, "abasic site" encompasses any chemical structure remaining following treatment of a canonical or non-canonical nucleotide (present in a polynucleotide chain) with an agent (e.g., an enzyme, or heat or basic conditions) capable of effecting cleavage of a base portion of a non-canonical nucleotide. Thus, an abasic site as used herein includes a modified sugar moiety attached to the 3' terminus of nicked polynucleotide, as when, for example, endonuclease III or OGG1 protein are used to cleave the base portion of the non-canonical nucleotide. See, e.g., Kow, (2000) *Methods* 22, 164-169 (e.g., FIG. 4).

As used herein, cleavage of a backbone (e.g., phosphodiester backbone) "at" an abasic site means cleavage of the phosphodiester linkage 3' to the abasic site or 5' to the abasic site, or both. As the disclosure herein conveys, "at" an abasic site refers to proximate or near location (such as immediately 3', immediately 5'). In still other embodiments, more complex forms of cleavage are possible, for example, cleavage such that cleavage of the phosphodiester backbone and cleavage of (a portion of) the abasic nucleotide results.

As used herein, a "label" (interchangeably called a "detectable moiety") refers to a moiety that is associated or linked with a polynucleotide (interchangeably called "labeling"). The labeled polynucleotide may be directly or indirectly detected, generally through a detectable signal. The detectable moiety (label) can be attached (or associated) either directly or through a non-interfering linkage group with other moieties capable of specifically associating with one or more sites to be labeled. The detectable moiety (label) may be covalently or non-covalently associated as well as directly or indirectly associated.

As used herein, a "blocked 3' end" refers to a 3' end of a polynucleotide fragment that contains a moiety, such as an aldehyde group, e.g., the sugar residue attached to the nucleotide base that was removed to create an abasic site, which is left behind at the 3' end of the polynucleotide as a result of cleaving a polynucleotide at the abasic site as described herein, rather than a hydroxyl group at the 3' end. "Unblocking" of the 3' end refers to removal of the non-nucleotide moiety, e.g., an aldehyde group, resulting in a polynucleotide having a hydroxyl group at the 3' end.

The following are examples of the methods of the invention. It is understood that various other embodiments may be practiced, given the general description provided herein. For example, reference to using an agent capable of cleaving a base portion of a non-canonical nucleotide means that any of the agents capable of cleaving a base portion of the non-canonical nucleotide described herein may be used.

Methods for Labeling and Fragmenting Nucleic Acids

The invention provides methods for generating fragments of nucleic acids. The methods generally comprise cleavage of the phosphodiester backbone of a polynucleotide comprising an abasic site at or near the abasic site, whereby a polynucleotide fragment comprising a blocked 3' end is generated; and contacting the polynucleotide fragment with an enzyme capable of unblocking the blocked 3' end of the fragment, whereby a polynucleotide fragment comprising a 3' hydroxyl group is generated. The polynucleotide comprising an abasic site may be produced by cleaving the base portion of a non-canonical nucleotide, a canonical nucleotide, or a methylated nucleotide. In some embodiments, the polynucleotide comprising an abasic site is cleaved at the abasic site with a polyamine, thereby producing a polynucleotide fragment comprising a blocked 3' end, wherein the blocked 3' end comprises a sugar aldehyde group from the nucleotide residue from which the abasic site was generated. In some embodiments, the polynucleotide fragment comprising a blocked 3' end is contacted with an enzyme comprising a 3' to 5' exonuclease activity, thereby unblocking the blocked 3' end (e.g., removing a sugar aldehyde group or other non-nucleotide moiety from the 3' end) to produce a polynucleotide fragment comprising a 3' hydroxyl group.

In one embodiment, the invention provides a method for fragmenting a polynucleotide comprising a blocked 3' end, comprising unblocking the blocked 3' end with an agent capable of unblocking the blocked 3' end of a polynucleotide, for example, an enzyme comprising a 3'-5' exonuclease activity as described herein. The polynucleotide comprising a blocked 3' end may be produced, for example, by cleaving a polynucleotide comprising an abasic site at or near the abasic site with an agent, for example, a polyamine, capable of cleaving a polynucleotide at or near an abasic site to produce a polynucleotide fragment comprising a blocked 3' end.

In some embodiments, polynucleotide fragments comprising 3' hydroxyl groups produced as described herein are labeled. In one embodiment, the polynucleotide fragment is labeled by extension at the 3' end with a template independent polymerase, resulting in addition of one or more labeled nucleotides (or nucleotides thereof) to the 3' end of the fragment. In one embodiment, the polynucleotide fragment is labeled by hybridizing the polynucleotide fragment to a polynucleotide template, extending from the 3' end with a template dependent polymerase, and incorporating labeled nucleotides into the extended polynucleotide fragment. In one embodiment, the polynucleotide fragment is labeled by ligation at the 3' end to a labeled polynucleotide with a ligase enzyme.

In one embodiment, a polynucleotide fragment comprising a 3' end hydroxyl group, produced as described herein, is extended from the 3' end using a template independent polymerase to produce a tailed 3' end which may comprises labeled and/or unlabeled nucleotides. Tailing of the fragment comprising a 3' end hydroxyl group may comprise polymerizing a plurality of dNTPs or ribo-NTPs at the 3' end.

For simplicity, individual steps of the labeling and fragmentation method are discussed below. It is understood, however, that the steps may be performed simultaneously and/or in varied order, as discussed herein.

Synthesis of a Polynucleotide Comprising a Non-Canonical Nucleotide

In some embodiments, methods of the invention comprise generation of a polynucleotide comprising an abasic site by cleaving the base portion of a non-canonical nucleotide in a polynucleotide comprising a non-canonical nucleotide. The polynucleotide comprising a non-canonical nucleotide may be produced by synthesizing a polynucleotide from a template in the presence of at least one non-canonical nucleotide (interchangeably termed "non-canonical deoxyribonucleoside triphosphate"), whereby a polynucleotide comprising a non-canonical nucleotide is generated. The frequency of incorporation of non-canonical nucleotides into the polynucleotide relates to the size of fragment produced using the methods of the invention because the spacing between non-canonical nucleotides in the polynucleotide comprising a non-canonical nucleotide, along with the reaction conditions used, determines the approximate size of the fragments resulting from generation of an abasic site from the non-canonical nucleotide and cleavage of the backbone at the abasic site, as described herein.

Generally, the polynucleotide is DNA, though, as noted herein, the polynucleotide can comprise altered and/or modified nucleotides, internucleotide linkages, ribonucleotides, etc. As generally used herein, it is understood that "DNA" applies to polynucleotide embodiments.

Methods for synthesizing polynucleotides, e.g., single and double stranded DNA, from a template are well known in the art, and include, for example, single primer isothermal amplification (SPIA™), Ribo-SPIA™, PCR, reverse transcription, primer extension, limited primer extension, replication (including rolling circle replication), strand displacement amplification (SDA), nick translation, multiple displacement amplification (MDA), rolling circle amplification (RCA) and, e.g., any method that results in synthesis of the complement of a template sequence such that at least one non-canonical nucleotide can be incorporated into a polynucleotide. See, e.g., Kurn, U.S. Pat. No. 6,251,639; Kurn, WO 02/00938; Kurn, U.S. Pat. No. 6,946,251, Kurn, U.S. Pat. No. 6,692,918; Mullis, U.S. Pat. No. 4,582,877; Wallace, U.S. Pat. No. 6,027,923; U.S. Pat. Nos. 5,508,178; 5,888,819; 6,004,744; 5,882,867; 5,710,028; 6,027,889; 6,004,745; 5,763,178; 5,011,769; see also Sambrook (1989) "Molecular Cloning: A Laboratory Manual", second edition; Ausebel (1987, and updates) "Current Protocols in Molecular Biology"; Mullis, (1994) "PCR: The Polymerase Chain Reaction". One or more methods known in the art can be used to generate a polynucleotide comprising a non-canonical nucleotide. It is understood that the polynucleotide comprising a non-canonical nucleotide can be single stranded or double stranded or partially double stranded, and that one or both strands of a double stranded polynucleotide can comprise a non-canonical nucleotide. For convenience, "DNA" is used herein to describe (and exemplify) a polynucleotide. Suitable methods include methods that result in one single- or double-stranded polynucleotide comprising a non-canonical nucleotide (for example, reverse transcription, production of double stranded cDNA, a single round of DNA replication), as well as methods that result in multiple single stranded or double stranded copies or copies of the complement of a template (for example, single primer isothermal amplification or Ribo-SPIA™ or PCR). In one embodiment, a single-stranded polynucleotide comprising a non-canonical nucleotide is synthesized using single primer isothermal amplification. See Kurn, U.S. Pat. Nos. 6,251,639 and 6,692,918.

Generally, the polynucleotide comprising a non-canonical nucleotide is generated from a template in the presence of all four canonical nucleotides and at least one non-canonical nucleotide under reaction conditions suitable for synthesis of polynucleotides, including suitable enzymes and primers, if necessary. Reaction conditions and reagents, including primers, for synthesizing the polynucleotide comprising a non-canonical nucleotide are known in the art, and further discussed herein. As described herein, non-canonical nucleotides are generally capable of polymerization (i.e., are substrates for DNA polymerase), and capable of being rendered abasic following treatment with a suitable agent capable of generally, specifically or selectively cleaving a base portion of a non-canonical nucleotide. Suitable non-canonical nucleotides are well-known in the art, and include: deoxyuridine triphosphate (dUTP), deoxyinosine triphosphate (dITP), 5-hydroxymethyl deoxycytidine triphosphate (5-OH-Me-dCTP). See, e.g., Jendrisak, U.S. Pat. No. 6,190,865 B1; Mol. Cell. Probes (1992) 251-6. Generally, in embodiments in which a polynucleotide comprising a non-canonical nucleotide serves as a template for further amplification (e.g., as when multiple copies of a double stranded polynucleotides comprising a non-canonical nucleotide are synthesized, e.g., by PCR amplification), a polynucleotide comprising a non-canonical nucleotide must be capable of serving as a template for further amplification.

It is understood that two or more different non-canonical nucleotides can be incorporated into the polynucleotide synthesized from the template by DNA polymerase, whereby a polynucleotide comprising at least two different non-canonical nucleotides is generated.

Conditions for limited and/or controlled incorporation of a non-canonical nucleotide are known in the art. See, e.g., Jendrisak, U.S. Pat. No. 6,190,865 B1; Mol. Cell. Probes (1992) 251-6; Anal. Biochem. (1993) 211:164-9; see also Sambrook (1989) "Molecular Cloning: A Laboratory Manual", second edition; Ausebel (1987, and updates) "Current Protocols in Molecular Biology". The frequency (or spacing) of non-canonical nucleotides in the resulting polynucleotide comprising a non-canonical nucleotide, and thus the average size of fragments generated using the methods of the invention (i.e., following cleavage of a base portion of a non-canonical nucleotide, and cleavage of a phosphodiester backbone at a non-canonical nucleotide), is controlled by variables known in the art, including: frequency of nucleotide(s) corresponding to the non-canonical nucleotide(s) in the template (or other measures of nucleotide content of a sequence, such as average G-C content), ratio of canonical to non-canonical nucleotide present in the reaction mixture; ability of the polymerase to incorporate the non-canonical nucleotide, relative efficiency of incorporation of non-canonical nucleotide verses canonical nucleotide, and the like. It is understood that the average fragmentation size also relates to the reaction conditions used during fragmentation, as is further discussed herein. The reaction conditions can be empirically determined, for example, by assessing average fragment size generated using the methods of the invention taught herein. The level of labeling at an abasic site also relates to the frequency of incorporation of non-canonical nucleotides, as is further discussed herein.

Generally, a non-canonical base can be incorporated at about every 5, 10, 15, 20, 25, 30, 40, 50, 65, 75, 85, 100, 123, 150, 175, 200, 225, 250, 300, 350, 400, 450, 500, 550, 600, 650 or more nucleotides apart in the resulting polynucleotide comprising a non-canonical nucleotide. In one embodiment, the non-canonical nucleotide is incorporated about every 200 nucleotides, about every 100 nucleotide, or about every 50 nucleotide. In another embodiment, the non-canonical nucleotide is incorporated about every 50 to about 200 nucleotides. In some embodiments, a 1:5 ratio of dUTP and dTTP is used in the reaction mixture.

The polynucleotide template (along which the polynucleotide comprising a non-canonical nucleotide is synthesized) may be any template from which labeled polynucleotide fragments are desired to be produced. As is evident from the description herein, the labeled polynucleotide fragments are the complement of the sequence of the polynucleotide template. The template includes double-stranded, partially double-stranded, and single-stranded nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Obtaining and purifying nucleic acids use standard techniques in the art. RNAs can be obtained and purified using standard techniques in the art. A DNA template (including genomic DNA template) can be transcribed into RNA form, which can be achieved using methods disclosed in Kurn, U.S. Pat. No. 6,251,639 B1, and by other techniques (such as expression systems) known in the art. RNA copies of genomic DNA would generally include untranscribed sequences generally not found in mRNA, such as introns, regulatory and control elements, etc. DNA copies of an RNA template can be synthesized using methods described in Kurn, U.S. Pat. No. 6,946,251 or other techniques known in the art). Synthesis of polynucleotide comprising a non-canonical nucleotide from a DNA-RNA hybrid can be accomplished by denaturation of the hybrid to obtain a ssDNA and/or RNA, cleavage with an agent capable of cleaving RNA from an RNA/DNA hybrid, and other methods known in the art. The template can be only a minor fraction of a complex mixture such as a biological sample and can be obtained from various biological material by procedures well known in the art. The template can be known or unknown and may contain more than one desired specific nucleic acid sequence of interest, each of which may be the same or different from each other. Therefore, the methods of the invention are useful not only for producing one specific polynucleotide comprising a non-canonical nucleotide, but also for producing simultaneously more than one different specific polynucleotides comprising a non-canonical nucleotide. The template DNA can be a sub-population of nucleic acids, for example, a subtractive hybridization probe, total genomic DNA, restriction fragments, a cDNA library, cDNA prepared from total mRNA, a cloned library, or amplification products of any of the templates described herein. In some cases, the initial step of the synthesis of the complement of a portion of a template nucleic acid sequence is template denaturation. The denaturation step may be thermal denaturation or any other method known in the art, such as alkali treatment.

For simplicity, the polynucleotide comprising a non-canonical nucleotide is described as a single nucleic acid. It is understood that the polynucleotide can be a single polynucleotide, or a population of polynucleotides (from a few to a multiplicity to a very large multiplicity of polynucleotides). It is further understood that a polynucleotide comprising a non-canonical nucleotide can be a multiplicity (from small to very large) of different polynucleotide molecules. Such populations can be related in sequence (e.g., member of a gene family or superfamily) or extremely diverse in sequence (e.g., generated from all mRNA, generated from all genomic DNA, etc.). Polynucleotides can also correspond to single sequence (which can be part or all of a known gene, for example a coding region, genomic portion, etc.). Methods, reagents, and reaction conditions for generating specific polynucleotide sequences and multiplicities of polynucleotide sequences are known in the art.

Suitable methods of synthesis of a polynucleotide comprising a non-canonical nucleotide are generally template-dependent (in the sense that polynucleotide comprising a non-canonical nucleotide is synthesized along a polynucleotide template, as generally described herein). It is understood that non-canonical nucleotides can be incorporated into a polynucleotide as a result of template-independent methods. For example, one or more primer(s) can be designed to comprise one or more non-canonical nucleotides. See, e.g., Richards, U.S. Pat. Nos. 6,037,152, 5,427,929, and 5,876,976. As discussed herein, inclusion of at least one non-canonical nucleotide in a primer results in cleavage of a base-portion of a non-canonical nucleotide and labeling at the abasic site (i.e., following generation of an abasic site, as described herein), thus generating a polynucleotide fragment or a labeled polynucleotide fragment comprising a portion of the primer. Inclusion of a non-canonical nucleotide in a primer may be particularly suitable for methods such as single primer isothermal amplification. See Kurn, U.S. Pat. No. 6,251,639 B1; Kurn, WO 02/00938; Kurn, U.S. Patent Publication No. 2003/0087251 A1. Non-canonical nucleotide(s) can also be added to a polynucleotide by template-independent methods such as tailing or ligation of a second polynucleotide comprising a non-canonical nucleotide. Methods for tailing and ligation are well-known in the art.

Cleavage of a Base Portion of a Nucleotide to Create an Abasic Site

In methods for fragmentation of polynucleotides as described herein, a polynucleotide comprising an abasic site is cleaved at or near the abasic site to generate a polynucleotide fragment with a blocked 3' end, and contacted with an enzyme capable of unblocking the blocked 3' end to generate a polynucleotide fragment with a 3' hydroxyl group. The polynucleotide comprising an abasic site may be generated by cleaving the base portion of a nucleotide to create an abasic site. In various embodiments, the nucleotide from which the base portion is cleaved to create an abasic site is a non-canonical nucleotide, a canonical nucleotide, or a methylated nucleotide.

Cleaving a Base Portion of a Non-Canonical Nucleotide to Create an Abasic Site

A polynucleotide comprising a non-canonical nucleotide is treated with an agent, such as an enzyme, capable of generally, specifically, or selectively cleaving a base portion of the non-canonical deoxyribonucleoside to create an abasic site. As used herein, "abasic site" encompasses any chemical structure remaining following removal of a base portion (including the entire base) with an agent capable of cleaving a base portion of a nucleotide, e.g., by treatment of a non-canonical nucleotide (present in a polynucleotide chain) with an agent (e.g., an enzyme, acidic conditions, or a chemical reagent) capable of effecting cleavage of a base portion of a non-canonical nucleotide. In some embodiments, the agent (such as an enzyme) catalyzes hydrolysis of the bond between the base portion of the non-canonical nucleotide and a sugar in the non-canonical nucleotide to generate an abasic site comprising a hemiacetal ring and lacking the base (interchangeably called "AP" site), though other cleavage products are contemplated for use in the methods of the invention. Suitable agents and reaction conditions for cleavage of base portions of non-canonical nucleotides are known in the art, and include: N-glycosylases (also called "DNA glycosylases" or "glycosidases") including Uracil N-Glycosylase ("UNG"; specifically cleaves dUTP) (interchangeably termed "uracil DNA glyosylase"), hypoxanthine-N-Glycosylase, and hydroxy-methyl cytosine-N-glycosylase; 3-methyladenine DNA glycosylase, 3- or 7-methylguanine DNA glycosylase, hydroxymethyluracil DNA glycosylase; T4 endonuclease V. See, e.g., Lindahl, *PNAS* (1974) 71(9):3649-3653; Jendrisak, U.S. Pat. No. 6,190,865 B1. In one embodiment, UNG is used to cleave a base portion of the non-canonical nucleotide.

Generally, cleavage of base portions of non-canonical nucleotides is general, specific or selective cleavage, in the sense that the agent (such as an enzyme) capable of cleaving a base portion of a non-canonical nucleotide generally, specifically or selectively cleaves the base portion of a particular non-canonical nucleotide, whereby greater than about 98%, about 95%, about 90%, about 85%, or about 80% of the base portions cleaved are base portions of non-canonical nucleotides. However, extent of cleavage can be less. Thus, reference to specific cleavage is exemplary. General, specific or selective cleavage is desirable for control of the fragment size in the methods of generating labeled polynucleotide fragments of the invention (i.e., the fragments generated by cleavage of the backbone at an abasic site). Generally, reaction conditions are selected such that the reaction in which the abasic site(s) are created can run to completion.

In some embodiments, the polynucleotide comprising a non-canonical nucleotide is purified following synthesis of the non-canonical polynucleotide (to eliminate, for example, residual free non-canonical nucleotides that are present in the reaction mixture). In other embodiments, there is no intermediate purification between the synthesis of the polynucleotide comprising the non-canonical nucleotide and subsequent steps (such as cleavage of a base portion of the non-canonical nucleotide and cleavage of a phosphodiester backbone at the abasic site).

As noted herein, for convenience, cleavage of a base portion of a non-canonical nucleotide (whereby an abasic site is generated) has been described as a separate step. It is understood that this step may be performed simultaneously with synthesis of the polynucleotide comprising a non-canonical nucleotide (as described above), cleavage of the backbone at an abasic site (fragmentation) and/or labeling at an abasic site.

It is understood that the choice of non-canonical nucleotide can dictate the choice of enzyme to be used to cleave the base portion of that non-canonical enzyme, to the extent that particular non-canonical nucleotides are recognized by particular enzymes that are capable of cleaving a base portion of the non-canonical nucleotide.

Cleaving a Base Portion of a Canonical Nucleotide to Create an Abasic Site

In another aspect, the invention comprises use of an agent, such as an enzyme, that cleaves a base portion of a canonical nucleotide, to generate a polynucleotide comprising an abasic site. In some embodiments, the agent is not capable of cleaving a methylated nucleotide.

In some embodiments, the agent is an enzyme. In one embodiment, the enzyme is cytosine deaminase. See Sohail et al, NAR 2003, 31: 2990-94. Cytosine deaminase catalyzes the deamination of cytosine, such that dUTP is generated. Cleavage of a base portion of dUTP is necessary to generate the abasic site. Thus, the invention encompasses use of (a) an agent (such as cytosine deaminase) that modifies a nucleotide (such as dCTP), whereby dUTP is generated, in conjunction with (b) an agent (such as an enzyme, such as UNG) that cleaves a base portion of dUTP, whereby an abasic site is generated. Methods for cleaving a base portion of dUTP are known in the art. See, e.g., Lindahl, PNAS (1974) 71(9): 3649-3653; Jendrisak, U.S. Pat. No. 6,190,865 B1; U.S. Pat. No. 5,035,996; U.S. Pat. No. 5,418,149; Sartori et al (2002) EMBO J. 21:3182-3191. As used herein, "in conjunction" encompasses simultaneous treatment (e.g., when cytosine deaminase and UNG cleavage occurs in the same reaction mixture) and/or treatment at different times (e.g., when cytosine deaminase and UNG treatment is conducted sequentially).

Generally, cleavage of the base portion of a canonical nucleotide is general, specific or selective cleavage (in the sense that the agent (such as an enzyme) capable of cleaving a base portion of a canonical nucleotide generally, specifically or selectively cleaves the base portion of a particular canonical nucleotide, whereby about any of 98%, 95%, 90%, 85%, or 80% of the base portions cleaved are base portions of canonical nucleotides. However, extent of cleavage can be less. Thus, reference to specific cleavage is exemplary.

It is understood that the frequency (or spacing) of abasic sites in the resulting polynucleotide comprising an abasic site (following cleavage of a base portion of a unmethylated nucleotide, and thus the average size of fragments generated using the methods of the invention (i.e., following cleavage of a phosphodiester backbone at an abasic site), is controlled by variables known in the art, including: frequency of the target canonical nucleotide(s) from which an abasic site will be generated in the polynucleotide (or other measures of nucleotide content of a sequence, such as average G-C content), length of the polynucleotide, and the reaction conditions used during generation of abasic site.

Cleaving a Base Portion of a Methylated Nucleotide to Create an Abasic Site

In aspects involving cleavage of a base portion of a methylated nucleotide to generate a polynucleotide comprising an abasic site, the polynucleotide comprising a methylated nucleotide (in some embodiments, suspected of comprising a methylated nucleotide) is treated with an agent, such as an enzyme, capable of generally, specifically, or selectively cleaving a base portion of the methylated deoxyribonucleoside to create an abasic site. As used herein, "abasic site" encompasses any chemical structure remaining following removal of a base portion (including the entire base) of a methylated nucleotide with an agent capable of cleaving a base portion of a methylated nucleotide, e.g., by treatment of a methylated nucleotide (present in a polynucleotide chain) with an agent (e.g., an enzyme) capable of effecting cleavage of a base portion of a methylated nucleotide. In some embodiments, the agent (such as an enzyme) catalyzes hydrolysis of the bond between the base portion of the methylated nucleotide and a sugar in the methylated nucleotide to generate an abasic site comprising a hemiacetal ring and lacking the base (interchangeably called "AP" site), though other cleavage products are contemplated for use in the methods of the invention. Generally, the methods involving cleavage of a base portion of a methylated nucleotide are suitable for use with polynucleotides comprising a low frequency of methylated nucleotides (i.e., generally, not hypermethylated regions, such a CpG islands and the like), though other uses are contemplated.

The polynucleotide comprising (in some embodiments, suspected of comprising) a methylated nucleotide is treated with an agent, such as an enzyme, capable of generally, specifically, or selectively cleaving a base portion of the methylated deoxyribonucleoside to create an abasic site. As used herein, "abasic site" encompasses any chemical structure remaining following removal of a base portion (including the entire base) of a methylated nucleotide with an agent capable of cleaving a base portion of a methylated nucleotide, e.g., by treatment of a methylated nucleotide (present in a polynucleotide chain) with an agent (e.g., an enzyme, acidic conditions, or a chemical reagent) capable of effecting cleavage of a base portion of a methylated nucleotide. In some embodiments, the agent (such as an enzyme) catalyzes hydrolysis of the bond between the base portion of the methylated nucleotide and a sugar in the canonical nucleotide to generate an abasic site comprising a hemiacetal ring and lacking the base (interchangeably called "AP" site), though other cleavage products are contemplated for use in the methods of the invention.

In some embodiments, the methylated nucleotide is 5-methylcytosine. In some embodiments, 5-methylcytosine is present as a methylated CpG dinucleotide. The CpG dinucleotide may be fully or hemi-methylated. In other embodiments, the methylated nucleotide is 3-methyladenine. In other embodiments, the methylated nucleotide is 7-methyladenine and/or 3-methylguanine.

Suitable agents and reaction conditions for cleavage of base portions of methylated nucleotides are known in the art, and include: 5-methylcytosine DNA glycosylase (5-MCDG), which cleaves the base portion of 5-methylcytosine (5-MeC) from the DNA backbone (Wolffe et al., Proc. Nat. Acad. Sci. USA 96:5894-5896, 1999); 3-methyladenosine-DNA glycosylase I, which cleaves the base portion of 3-methyl adenosine from the DNA backbone (see, e.g. Hollis et al (2000) Mutation Res. 460: 201-210); and/or 3-methyladenosine DNA glycosylase II, which cleaves the base portion of 3-methyladenosine, 7-methylguanine, 7-methyladenosine, and/3-methylguanine from the DNA backbone. See McCarthy et al (1984) EMBO J. 3:545-550. Multifunctional and mono-functional forms of 5-MCDG have been described. See Zhu et al., Proc. Natl. Acad. Sci. USA 98:5031-6, 2001; Zhu et al., Nuc. Acid Res. 28:4157-4165, 2000; and Nedderrnann et al., J. B. C. 271:12767-74, 1996 (describing bifunctional 5-MCDG; Vairapandi & Duker, Oncogene 13:933-938, 1996; Vairapandi et al., J. Cell. Biochem. 79:249-260, 2000 (describing mono-functional enzyme comprising 5-MCDG activity). In some embodiments, 5-MCDG preferentially cleaves fully methylated polynucleotide sites (e.g., CpG dinucleotides), and in other embodiments, 5-MCDG preferentially cleaves a hemi-methylated polynucleotide. For example, mono-functional human 5-methylcytosine DNA glycosylase cleaves DNA specifically at fully methylated CpG sites, and is relatively inactive on hemimethylated DNA (Vairapandi & Duker, supra; Vairapandi et al., supra). By contrast, chick embryo 5-methylcytosine-DNA glycosylase has greater activity directed to hemimethylated methylation sites. In some embodiments, the activity of 5-MCDG is potentiated (increased or enhanced) with accessory factors, such as recombinant CpG-rich RNA, ATP, RNA helicase enzyme, and proliferating cell nuclear antigen (PCNA). See U.S. Patent Publication No. 20020197639 A1. One or more agents may be used. In some embodiments, the one or more agents cleave a base portion of the same methylated nucleotide. In other embodiments, the one or more agents cleave a base portion of different methylated nucleotides. Treatment with two or more agents may be sequential or simultaneous.

As is evident, in some embodiments, dUTP is generated as an intermediate and cleavage of a base portion of dUTP is necessary to generate the abasic site. Methods for cleaving a base portion of dUTP are known in the art. See, e.g., Lindahl, PNAS (1974) 71(9):3649-3653; Jendrisak, U.S. Pat. No. 6,190,865 B1; U.S. Pat. No. 5,035,996; U.S. Pat. No. 5,418,149; Sartori et al (2002) EMBO J. 21:3182-3191. Thus, in some embodiments, an agent that cleaves a base portion of a methylated nucleotides (such as an enzyme, such as 5-MCDG) is used in conjunction with UNG to generate an abasic site from the methylated nucleotide. As used herein, "in conjunction" encompasses simultaneous treatment (e.g., when 5-MCDG and UNG cleavage occurs in the same reaction mixture) and/or treatment at different times (e.g., when 5-MCDG and UNG treatment is conducted sequentially).

In some embodiments, cleavage of the base portion of the methylated nucleotides is general, specific or selective cleavage (in the sense that the agent (such as an enzyme) capable of cleaving a base portion of a methylated nucleotide generally, specifically or selectively cleaves the base portion of a particular methylated nucleotide), whereby about any of 98%, 95%, 90%, 85%, or 80% of the base portions cleaved are base portions of methylated nucleotides. However, extent of cleavage can be less. Thus, reference to specific cleavage is exemplary.

It is understood that the frequency (or spacing) of abasic sites in the resulting polynucleotide comprising an abasic site (following cleavage of a base portion of a methylated nucleotide, and thus the average size of fragments generated using the methods of the invention (i.e., following cleavage of a phosphodiester backbone at an abasic site), is controlled by variables known in the art, including: frequency of methylated nucleotide(s) in the polynucleotide (or other measures of nucleotide content of a sequence, such as average G-C content), length of the polynucleotide comprising a methylated nucleotide, and the reaction conditions used during generation of abasic site, as is further discussed herein.

Cleaving the Backbone at or Near the Abasic Site to Generate a Polynucleotide Fragment with a Blocked 3' End The backbone of the polynucleotide comprising an abasic site is cleaved at or near the abasic site with an agent that generates a polynucleotide fragment with a blocked 3' end. It is understood that cleavage of the base portion of a nucleotide to create an abasic site and cleavage of the polynucleotide backbone can be performed simultaneously. For convenience, however, these reactions are described as separate steps.

Following generation of an abasic site by cleavage of the base portion of a nucleotide, for example, a non-canonical nucleotide present in the polynucleotide, the backbone of the polynucleotide is cleaved at or near the abasic site, for example, the site of incorporation of a non-canonical nucleotide (also termed the abasic site, following cleavage of the base portion of the non-canonical nucleotide), with an agent capable of effecting cleavage of the backbone at the abasic site to generate a polynucleotide fragment comprising a blocked 3' end. Cleavage of the polynucleotide backbone (also termed "fragmentation") results in at least two fragments (depending on the number of abasic sites present in the polynucleotide comprising an abasic site, and the extent of cleavage), one of which does not comprise a blocked 3' end.

Suitable agents (for example, an enzyme, a chemical and/or reaction conditions such as heat) capable of cleavage of the backbone at an abasic site to generate a polynucleotide fragment with a blocked 3' end are well known in the art, and include: heat treatment and/or chemical treatment (including basic conditions, acidic conditions, alkylating conditions, or amine mediated cleavage of abasic sites, (see e.g., McHugh and Knowland, *Nucl. Acids Res.* (1995) 23(10):1664-1670; Bioorgan. Med. Chem. (1991) 7:2351; Sugiyama, Chem. Res. Toxicol. (1994) 7: 673-83; Horn, *Nucl. Acids. Res*., (1988) 16:11559-71). As used herein, "agent" encompasses reaction conditions such as heat. In another embodiment, cleavage is with a polyamine, such as N,N'-dimethylethylenediamine (DMED). See, e.g. McHugh and Knowland, supra.

Generally, cleavage is between the nucleotide immediately 3' to the abasic residue and the abasic residue. As is well known in the art, cleavage can be 3' to the abasic site (e.g., cleavage between the deoxyribose ring and 3'-phosphate group of the abasic residue and the deoxyribose ring of the adjacent nucleotide, generating a free 5' phosphate group on the deoxyribose ring of the adjacent nucleotide), such that an abasic site is located at the 3' end of the resulting fragment. Treatment under basic conditions or with amines (such as N,N'-dimethylethylenediamine) results in cleavage of the phosphodiester backbone immediately 3' to the abasic site to produce a polynucleotide fragment with a blocked 3' end. In addition, more complex forms of cleavage are also possible, for example, cleavage such that cleavage of the phosphodiester backbone and cleavage of (a portion of) the abasic nucleotide results. For example, under certain conditions, cleavage using chemical treatment and/or thermal treatment may comprise a β-elimination step which results in cleavage of a bond between the abasic site deoxyribose ring and its 3' phosphate, generating a reactive α,β-unsaturated aldehyde which can be labeled or can undergo further cleavage and cyclization reactions. See, e.g. Sugiyama, *Chem. Res. Toxicol.* (1994) 7: 673-83; Horn, *Nucl. Acids. Res.*, (1988) 16:11559-71. It is understood that more than one method of cleavage can be used, including two or more different methods which result in multiple, different types of cleavage products comprising blocked 3' ends.

Generally, cleavage of the backbone at an abasic site is general, specific or selective cleavage, whereby greater than about 98%, about 95%, about 90%, about 85%, or about 80% of the cleavage is at an abasic site. However, extent of cleavage can be less. Thus, reference to specific cleavage is exemplary. General, specific or selective cleavage is desirable for control of the fragment size in the methods of generating labeled polynucleotide fragments of the invention. In some embodiments, reaction conditions can be selected such that the cleavage reaction is performed in the presence of a large excess of reagents and allowed to run to completion with minimal concern about excessive cleavage of the polynucleotide (i.e., while retaining a desired fragment size, which may be determined by spacing of incorporated non-canonical nucleotides, during the synthesis step, above). In other embodiments, extent of cleavage can be less, such that polynucleotide fragments are generated comprising an abasic site at an end and an abasic site(s) within or internal to the polynucleotide fragment (i.e., not at an end).

As noted herein, in embodiments in which an abasic site is generated by cleavage of a base portion of a non-canonical nucleotide in a polynucleotide synthesized in the presence of a non-canonical nucleotide, the frequency of incorporation of non-canonical nucleotides into the polynucleotide relates to the size of fragment produced using the methods of the invention because the spacing between non-canonical nucleotides in the polynucleotide comprising a non-canonical nucleotide, as well as the reaction conditions selected, determines the approximate size of the resulting fragments (following cleavage of a base portion of a non-canonical nucleotide, whereby an abasic site is generated, and cleavage of the backbone at the abasic site as described herein).

In methods of the invention, suitable fragment sizes are generally about 5, 10, 15, 20, 25, 30, 40, 50, 65, 75, 85, 100, 123, 150, 175, 200, 225, 250, 300, 350, 400, 450, 500, 550, 600, 650 or more nucleotides in length. In some embodiments, the fragment is about 200 nucleotides, about 100 nucleotides, or about 50 nucleotides in length. In another embodiment, the size of a population of fragments is about 50 to 200 nucleotides. It is understood that the fragment size is approximate, particularly when populations of fragments are generated, because the incorporation of a non-canonical nucleotide (which relates to the fragment size following cleavage) will vary from template to template, and also between copies of the same template. Thus, fragments generated from same starting material (such as a single polynucleotide template) may have different (and/or overlapping) sequence, while still having the same approximate size or size range.

Following cleavage of the polynucleotide backbone at the abasic site, every fragment will comprise one abasic site (if cleavage is completely efficient), except for the 3'-most fragment, which will lack an abasic site. All other fragments will comprise a 3' abasic site (a blocked 3' end).

Unblocking of the Blocked 3' End to Generate a Polynucleotide Fragment with a 3' Hydroxyl Group A polynucleotide fragment comprising a blocked 3' end, prepared as described herein, is contacted with an enzyme capable of unblocking the blocked 3' end, whereby a polynucleotide fragment comprising a 3' hydroxyl group is generated. In some embodiments, the enzyme capable of unblocking the blocked 3' end comprises a 3' to 5' exonuclease activity, generally a non-processive activity. In some embodiments, the enzyme that comprises a 3' to 5' exonuclease activity does not comprise an endonuclease activity, although an enzyme comprising an endonuclease activity may also be used, under conditions in which the endonuclease activity is minimized or absent. In some embodiments, the enzyme comprising a 3' to 5' exonuclease activity is selected from the group consisting of endonuclease 4, exonuclease T, and APE 1.

Various 3'-5' exonucleases may be used for removal of the 3' blocking group following fragmentation of a polynucleotide comprising an abasic site with an agent, such as a polyamine, for example, DMED, that produces a fragment with a blocked 3' end. A review of 3'-5' exonucleases is presented in Shevelev et al. (2002) *Nature Reviews Molecular Cell Biology* 3:367-376. Many DNA repair related exonucleases have been discovered in recent years in addition to APE1 and homologous AP nucleases in other eukaryotes and prokaryotes. Of special interest are the TREX1 and two 3'-5' exonucleases capable of unblocking a blocked polynucleotide 3' terminus, as described in Mazur et al., *J. Biol. Chem.* 276(20):17033-17029. Another effective exonuclease is APE2, which efficiently removes 3' blocking groups from polynucleotide 3' termini, as described in Burkovics et al. (2006) *Nucleic Acids Res.* 34(9):2508-2515.

In some embodiments, an important feature of the 3'-5' exonuclease is the ability to remove a blocking group at the 3' terminus of a single stranded polynucleotide (such as a single stranded amplification product). In some embodiments, the exonuclease is non-processive. An example of such a non-processive exonuclease is human TREX2 3'-5' exonuclease, as described in Perrino et al., *J. Biol. Chem.* 280(15): 15212-15218.

Polymerase Extension or Ligation of Polynucleotide Fragments with 3' Hydroxyl Groups A polynucleotide fragment with an unblocked 3' end, prepared as described herein, may be extended from the hydroxyl group at the 3' end by a template independent or template dependent polymerase or may be ligated at the 3' end to another polynucleotide with a ligase enzyme.

In one embodiment, a polynucleotide fragment with an unblocked 3' end, prepared as described herein, is extended from the 3' hydroxyl group with a template independent polymerase, such as TdT, to incorporate one or more nucleotides, for example, one or more detectable nucleotides, at the 3' end of the polynucleotide fragment. In some embodiments, a labeled nucleotide is incorporated. In one embodiment, the labeled nucleotide is a biotinylated nucleotide, such as a biotinylated triphosphate (NTP), deoxynucleotide triphosphate (dNTP), or dideoxynucleotide triphosphate (ddNTP). For example, biotin 2'3'-dideoxy-UTP or biotin 2',3'-dideoxy-CTP may be incorporated at the 3' end of the polynucleotide fragment with TdT. In another embodiment, the labeled nucleotide comprises a fluorophore (e.g., cy dyes, alexa dyes, fluorescein, and other fluorophores known in the art). In other embodiments, the incorporated detectable nucleotide comprises an enzyme, a chromophore, a radiolabel, or a hapten which is detectable by binding of a labeled second member of a binding pair, such as, for example, biotin/ avidin or streptavidin, antigen/antibody, and the label attached to the second member of the binding pair may comprise, for example, a fluorophore, an enzyme, a chromophore, a radiolabel, or may be attached to a detectable particle. In one embodiment, the labeled nucleotide is a biotinylated nucleotide, for example, biotin 2',3'-dideoxy-UTP or 2',3'-dideoxy-CTP, and is detectable by binding of labeled avidin or streptavidin. In some embodiments, a polynucleotide fragment prepared in accordance with methods described herein is tailed with unlabeled nucleotides or a mixture of labeled and unlabeled nucleotides with a template independent polymerase such as TdT.

In another embodiment, a polynucleotide fragment with an unblocked 3' end, prepared as described herein, is hybridized to a polynucleotide template and extended from the 3' hydroxyl group with a template dependent polymerase. In one embodiment, the polynucleotide fragment with an unblocked 3' end is used as a primer to initiate synthesis of a polynucleotide complementary to the template. In one embodiment, the polynucleotide fragment is extended in the presence of one or more labeled nucleotides, such as one or more nucleotides attached to a member of a binding pair that is detectable by binding of a labeled second member of the binding pair, as described above, to produce a detectable polynucleotide.

In another embodiment, a polynucleotide fragment with an unblocked 3' end, prepared as described herein, is ligated at the 3' hydroxyl group to another polynucleotide using a ligase enzyme. In some embodiments, the polynucleotide to which the polynucleotide fragment is ligated comprises one or more detectable nucleotides as described above, resulting in a detectable ligated polynucleotide comprising the polynucleotide fragment with the unblocked 3' end and the polynucleotide to which the fragment was ligated.

As discussed above, a "label" can be directly detectable, or the label can be indirectly detectable, such as, for example, when the label is covalently or non-covalently associated with another moiety which is itself detectable. For example, biotin can be attached to nucleotide, which may be detected by binding to detectable avidin or streptavidin. In another example, an antibody (that can be detectably labeled) binds to a cognate antigen that is attached to a nucleotide. In some embodiments, the label comprises an organic molecule, a hapten, or a particle (such as a polystyrene bead). In some embodiments, the label is detected using antibody binding, biotin binding, or via fluorescence or enzyme activity. In some embodiments, the detectable signal is amplified.

In some embodiments, labeled polynucleotide fragments are produced which each comprise a single label, for example, incorporation of a detectable nucleotide at the 3' hydroxyl group with terminal transferase. This aspect is useful in quantitating level of hybridization, because signal is proportional to number of bound fragments, and does not relate to the length of the hybridizing fragment or the number of labels per fragment. Thus, hybridization intensity can generally be directly compared, regardless of fragment length. This offers an advantage over prior art methods in which nucleic acid fragments are labeled with multiple detectable moieties, e.g., incorporation of labeled nucleotides, and other methods of directly and indirectly detecting incorporated nucleotides. These methods generally result in multiple labels per hybridizing fragment, and thus are generally less suitable for quantitative applications. Multiple labels per nucleic acid can result in quenching, and potential interference with hybridization kinetics (due to the presence of multiple labeled moieties per nucleic acid).

Methods of signal detection are known in the art. Signal detection may be visual or utilize a suitable instrument appropriate to the particular label used, such as a spectrometer, fluorimeter, or microscope. For example, where the label is a radioisotope, detection can be achieved using, for example, a scintillation counter, or photographic film as in autoradiography. Where a fluorescent label is used, detection may be by exciting the fluorochrome with the appropriate wavelength of light and detecting the resulting fluorescence, such as by microscopy, visual inspection or photographic film, fluorometer, CCD cameras, scanner and the like. Where enzymatic labels are used, detection may be by providing appropriate substrates for the enzyme and detecting the resulting reaction product. For example, many substrates of horseradish peroxidase, such as o-phenylenediamine, give colored products. Simple colorimetric labels can usually be detected by visual observation of the color associated with the label; for example, conjugated colloidal gold is often pink to reddish, and beads appear the color of the bead. Instruments suitable for high sensitivity detection are known in the art.

It is understood that the polynucleotide or polynucleotide fragments can be additionally labeled using other methods known in the art, such as incorporation of labeled nucleotide analogs during synthesis of a polynucleotide comprising a non-canonical nucleotide, from which a polynucleotide comprising an abasic site is generated. In addition, following cleavage of the phosphodiester backbone of the polynucleotide comprising an abasic site, the 3' most fragment will lack an abasic site, (in embodiments in which the fragmentation reaction goes to completion). However, if polynucleotide synthesis step requires primer(s), a labeled primer(s) can be used such that the resulting fragment comprising a primer is labeled. Suitable labels and methods of labeling primers are known. In addition, a primer comprising a non-canonical nucleotide can be used. Following generation of an abasic site, cleavage of the phosphodiester backbone at the abasic site, and labeling at the abasic site, the fragment comprising at least a portion of the primer will be labeled.

Reaction Conditions and Detection

Appropriate reaction media and conditions for carrying out the methods of the invention include those that permit cleavage of a polynucleotide comprising an abasic site with an agent capable of cleaving a polynucleotide to produce a polynucleotide fragment with a blocked 3' end, and unblocking of a blocked 3' end with an agent capable of unblocking the 3' end of a polynucleotide to produce a polynucleotide comprising a 3' end hydroxyl group.

Appropriate reaction media and conditions for carrying out the cleavage of the phosphodiester backbone at an abasic site according to the methods of the invention are those that permit cleavage of the phosphodiester backbone at or near an abasic site to produce a polynucleotide fragment comprising a blocked 3' end. Such media and conditions are known to persons of skill in the art, and are described in various publications, such as *Bioorgan. Med. Chem.* (1991) 7:2351; Sugiyama, *Chem. Res. Toxicol.* (1994) 7: 673-83; Horn, *Nucl. Acids. Res.*, (1988) 16:11559-71); Lindahl, *PNAS* (1974) 71(9):3649-3653; Jendrisak, U.S. Pat. No. 6,190,865 B1; Shida, *Nucleic Acids Res.* (1996) 24(22):4572-76; Srivastava, *J. Biol. Chem.* (1998) 273(13):21203-209; Carey, *Biochem.* (1999) 38:16553-60; *Chem Res Toxicol* (1994) 7:673-683. A reaction mixture suitable for simultaneous UNG treatment and N,N'-dimethylethylenediamine treatment is described in Example 4 of U.S. Patent Application No. 2004/0005614.

In another example, nucleic acids containing abasic sites are heated in a buffer solution containing an amine, for example, 25 mM Tris-HCl and 1-5 mM magnesium ions, for 10-30 minutes at 70° C. to 95° C. Alternatively, 1.0 M piperidine (a base) is added to polynucleotide comprising an abasic site which has been precipitated with ethanol and vacuum dried. The solution is then heated for 30 minutes at 90° C. and lyophilized to remove the piperidine. In another example, cleavage is effected by treatment with basic solution, e.g., 0.2 M sodium hydroxide at 37° for 15 minutes. See Nakamura (1998) *Cancer Res.* 58:222-225. In yet another example, incubation at 37 C with 100 mM N,N'-dimethylethylenediamine acetate, pH 7.4 is used to cleave. See McHugh and Knowland, (1995) *Nucl. Acids Res.* 23(10) 1664-1670.

In some embodiments, nucleic acid synthesis is performed to produce the polynucleotide to be fragmented. Appropriate media and conditions are known to persons of skill in the art, and are described in various publications, such as U.S. Pat. Nos. 6,190,865; 5,554,516; 5,716,785; 5,130,238; 5,194,370; 6,090,591; 5,409,818; 5,554,517; 5,169,766; 5,480,784; 5,399,491; 5,679,512; PCT Pub. No. WO99/42618; *Mol. Cell. Probes* (1992) 251-6; and *Anal. Biochem.* (1993) 211: 164-9. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method (if any) can also be included. Any aspect of the methods of the invention can occur at the same or varying temperatures. The synthesis reactions (particularly, primer extension other than the first and second strand cDNA synthesis steps, and strand displacement) can be performed isothermally, which avoids the cumbersome thermocycling process. The synthesis reaction is carried out at a temperature that permits hybridization of the oligonucleotides (primer) of the invention to the template polynucleotide and primer extension products, and that does not substantially inhibit the activity of the enzymes employed. The temperature can be in the range of preferably about 25° C. to about 85° C., more preferably about 30° C. to about 80° C., and most preferably about 37° C. to about 75° C. In some embodiments that include RNA transcription, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

In embodiments in which the polynucleotide comprising an abasic site is produced from a polynucleotide comprising a non-canonical nucleotide, Nucleotides, including non-canonical nucleotides (or other nucleotide analogs), that can be employed for synthesis of the nucleic acid comprising a non-canonical nucleotide in the methods of the invention are provided in the amount of from preferably about 50 to about 2500 μM, more preferably about 100 to about 2000 μM, even more preferably about 200 to about 1700 μM, and most preferably about 250 to about 1500 μM. The oligonucleotide components of the synthesis reactions of the invention are generally in excess of the number of template nucleic acid sequence to be replicated. They can be provided at about or at least about any of the following: 10, $10^2$, $10^4$, $10^6$, $10^8$, $10^{10}$, $10^{12}$ times the amount of target nucleic acid. Composite primers can be provided at about or at least about any of the following concentrations: 50 nM, 100 nM, 500 nM, 1000 nM, 2500 nM, 5000 nM.

Optionally, the polynucleotide comprising a non-canonical nucleotide can be treated with hydroxylamine (or any other suitable agent) to remove any aldehydes that may have formed spontaneously in the nucleic acid. See, e.g., Makrogiorgos, WO00/39345.

For convenience, the synthesis of a polynucleotide comprising a non-canonical nucleotide, and the cleavage of a base portion of that polynucleotide by an enzyme capable of cleaving a base portion of the non-canonical nucleotide, and the cleavage of the phosphodiester backbone at the abasic site, are described as separate steps. It is understood that these steps may be performed simultaneously, except (generally) in the case when a polynucleotide comprising a non-canonical nucleotide must be capable of serving as a template for further amplification (as in exponential methods of amplification, e.g. PCR).

Appropriate reaction media and conditions for carrying out the cleavage of a base portion of a non-canonical nucleotide according to the methods of the invention are those that permit cleavage of a base portion of a non-canonical nucleotide. Such media and conditions are known to persons of skill in the art, and are described in various publications, such as Lindahl, *PNAS* (1974) 71(9):3649-3653; Jendrisak, U.S. Pat. No. 6,190,865 B1; U.S. Pat. No. 5,035,996; U.S. Pat. No. 5,418,149. For example, buffer conditions can be as described above with respect to polynucleotide synthesis. In one embodiment, UNG (Epicentre Technologies, Madison Wis.) is added to a nucleic acid synthesis reaction mixture, and incubated at 37° C. for 20 minutes. In one embodiment, the reaction conditions are the same for the synthesis of a polynucleotide comprising a non-canonical nucleotide and the cleavage of a base portion of the non-canonical nucleotide. In another embodiment, different reaction conditions are used for these reactions. In some embodiments, a chelating regent (e.g. EDTA) is added before or concurrently with UNG in order to prevent the polymerase from extending the ends of the cleavage products.

In some embodiments, some of the components for performing a method as described herein are added simultaneously at various timepoints. In one embodiment, components for cleaving a base portion of a nucleotide to generate a polynucleotide comprising an abasic site and components for cleaving the phosphodiester backbone of the polynucleotide comprising the abasic site may be combined for simultaneous reaction. In one embodiment, components for cleaving a base portion of a nucleotide to generate a polynucleotide comprising an abasic site, components for cleaving the phosphodiester backbone of the polynucleotide comprising the abasic site, and components for unblocking a blocked 3' end may be combined for simultaneous reaction. In one embodiment, components for cleaving the phosphodiester backbone of a polynucleotide comprising the abasic site, and components for unblocking a blocked 3' end may be combined for simultaneous reaction. Such components may be added in any order at appropriate timepoints. Such timepoints can be readily identified by a person of skill in the art. In these embodiments, the reaction conditions and components may be varied between the different reactions.

The fragmenting or fragmenting and labeling process can be stopped at various timepoints, and resumed at a later time. Said timepoints can be readily identified by a person of skill in the art. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme or other reagent. In some embodiments, one or more of the components of the reactions is replenished prior to, at, or following the resumption of the reactions. Alternatively, the reaction can be allowed to proceed (i.e., from start to finish) without interruption.

The reaction can be allowed to proceed without purification of intermediate reaction products. Alternatively, products can be purified at various timepoints, conditions for which can be readily identified by a person of skill in the art.

Compositions

The invention also provides compositions and kits used in the methods described herein. The compositions may comprise any component(s), reaction mixture(s) and/or intermediate(s) described herein, as well as any combination thereof. For example, in one embodiment, the invention provides a composition comprising an agent capable of cleaving a base portion of a nucleotide to generate an abasic site in a polynucleotide, an agent capable of cleaving a phosphodiester backbone at or near an abasic site to produce a polynucleotide fragment with a blocked 3' end, and an enzyme capable of unblocking a blocked 3' end to generate a polynucleotide comprising a 3' hydroxyl group. In one embodiment, the agent capable of cleaving a base portion of a nucleotide to generate an abasic site is an N-glycosylase, for example, UNG. In one embodiment, the agent capable of cleaving a phosphodiester backbone at or near the abasic site is a polyamine, for example, DMED. In one embodiment, the enzyme capable of unblocking a blocked 3' end comprises a 3'-5' exonuclease activity, preferably a non-processive exonuclease activity, for example, endonuclease 4, exonuclease T, or APE1. Compositions of the invention may also comprise buffers, co-factors, or other components for carrying out the reactions of the methods described herein.

The invention also provides a composition comprising a polynucleotide fragment produced by a method as described herein and a template independent polymerase, a template dependent polymerase, or a ligase. In one embodiment, the invention provides a composition comprising a polynucleotide fragment produced as described herein, a template independent polymerase, for example, TdT, and a labeled nucleotide, an unlabeled nucleotide, or a mixture or labeled and unlabeled nucleotides. In one embodiment, the invention provides a composition comprising a polynucleotide fragment produced as described herein, a template dependent polymerase, and a polynucleotide template to which the polynucleotide fragment is capable of hybridizing, optionally further comprising nucleotides for polymerization, e.g., labeled, unlabeled, or a mixture of labeled and unlabeled nucleotides. In one embodiment, the composition comprises a complex comprising the polynucleotide fragment hybridized to a polynucleotide template. In one embodiment, the invention provides a composition comprising a polynucleotide fragment prepared as described herein, a ligase enzyme, and a polynucleotide to which the polynucleotide fragment is desired to be ligated.

The compositions are generally in lyophilized or in a suitable medium, such as aqueous form (if appropriate), preferably in a suitable buffer.

The invention also provides polynucleotide fragments and labeled polynucleotide fragments produced by any of the methods described herein, and compositions comprising such fragments. Accordingly, the invention provides a population of fragmented or fragmented and labeled polynucleotides, which are produced by any of the methods described herein (or compositions comprising the products).

The invention also provides reaction mixtures (or compositions comprising reaction mixtures) which contain various combinations of components described herein. Examples of reaction mixtures have been described. In one embodiment, the reaction mixture comprises a polynucleotide comprising an abasic site, and an agent (such as UNG) that is capable of cleaving a base portion from a non-canonical nucleotide, an agent (such as an amine, such as N,N'-dimethylethylenediamine) capable of cleaving the phosphodiester back at an abasic site, and an enzyme capable of unblocking a blocked 3' end of a polynucleotide. In one embodiment, the invention provides a reaction mixture comprising (a) UNG; (b) N,N'-dimethylethylenediamine; and (c) APE1.

Kits

The invention also provides kits for carrying out the methods of the invention. Accordingly, a variety of kits are provided in suitable packaging. The kits may contain instructions for carrying out any of the methods described herein for production of polynucleotide fragments or labeled polynucleotide fragments, or for one or more of the following applications using polynucleotide fragments prepared as described herein: methods of producing a hybridization probe; characterizing and/or quantitating nucleic acid; detecting a mutation; preparing a subtractive hybridization probe; detection (using a hybridization probe); and determining a gene expression profile, using the fragmented nucleic acids generated by the methods of the invention. The kits of the invention comprise one or more containers comprising any combination of the components described herein, and the following are examples of such kits.

In one embodiment, a kit of the invention comprises an agent capable of cleaving a base portion of a nucleotide to generate abasic site in a polynucleotide, an agent capable of cleaving a phosphodiester backbone of a polynucleotide at or near an abasic site to produce a polynucleotide fragment with a blocked 3' end, and an enzyme capable of unblocking the blocked 3' end to produce a polynucleotide fragment comprising a 3' end hydroxyl group. The kit may further comprise an agent capable of labeling the polynucleotide fragment comprising a 3' end hydroxyl group and/or a label to be incorporated into an extension or ligation product of the polynucleotide fragment. In one embodiment, the kit further comprises an enzyme capable of extending the 3' end of the polynucleotide fragment in a template independent or template dependent manner and optionally further comprises nucleotide substrates for such enzymes, either labeled or unlabeled or a mixture of labeled and unlabeled nucleotides. In one embodiment, the kit further comprises a ligase enzyme. In one embodiment, the kit comprises UNG, DMED, and APE1, and optionally further comprises TdT. In one embodiment, the kit further comprises components for synthesis of a polynucleotide to be fragmented, such as a primer, for example, a composite primer, and/or nucleotides, for example, canonical and/or non-canonical nucleotides.

Kits may also include one or more suitable buffers (as described herein) or any other necessary reagents for carrying out the reactions of the methods described herein. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the invention for the intended methods of the invention, and/or, as appropriate, for using the products for purposes such as, for example preparing a hybridization probe, expression profiling, preparing a microarray, or characterizing a nucleic acid. The instructions included with the kit generally include information as to reagents (whether included or not in the kit) necessary for practicing the methods of the invention, instructions on how to use the kit, and/or appropriate reaction conditions. Instructions may be in the form of printed media, electronic media, or a reference to a website address where instructions may be obtained.

The component(s) of the kit may be packaged in any convenient, appropriate packaging. The components may be packaged separately, or in one or multiple combinations.

The relative amounts of the various components in the kits can be varied widely to provide for concentrations of the reagents that substantially optimize the reactions that need to occur to practice the methods disclosed herein and/or to further optimize the sensitivity of any assay.

Tailing of the Fragmented Polynucleotide and Subsequent Isothermal Single Primer Amplification (SPIA™)

Fragmented polynucleotides may be tailed and subsequently amplified using the previously-described SPIA™ amplification procedure (U.S. Pat. Nos. 6,251,639 and 6,692,918).

Single stranded cDNA may be produced in the presence of non-canonical nucleotides, for example, amplified from RNA or DNA (e.g., amplified from RNA by the previously-described Ribo-SPIA™ method (U.S. Pat. No. 6,946,251)) or amplified from DNA by the SPIA™ method (U.S. Pat. Nos. 6,251,639 and 6,692,918), or generated without amplification by random priming or poly-A initiated reverse transcription using primers with or without a 5'-end tails (which can be RNA, for example, in a chimeric primer, or DNA). Single stranded cDNA is produced in the presence of non-canonical nucleotides and subsequently fragmented using a method of the invention as described herein. The fragmented single stranded DNA generated by the method of the invention comprises a 3'-hydroxyl terminus which can be extended by the template independent DNA synthesis using terminal transferase. Tailing of DNA using terminal transferase is well known in the art. The addition of homopolymeric tails, with deoxyribonucleotides has been previously described and is widely used for manipulation of cDNA (see, e.g., G Deng et al. (1981) *Nucleic Acids Res.* 9(16): 4173-4188; Schmidt et al., *Nucleic Acids Res.* 24(9) 1789-1791; Albuquerque-Silva et al., *Nucleic Acids Research* 26(13): 3314-3316; U.S. Pat. No. 6,406,890). Tailing at the 3'-end of a polynucleotide comprising a 3' end hydroxyl group using terminal transferase is widely used in molecular biology and commercial reagents and kits for various manipulations, including cDNA cloning, are readily available.

It is desirable to generate cDNA copies of single stranded, fragmented cDNA for further analysis, especially for analysis based on hybridization to probes which are designed for hybridization to the second strand cDNA (hybridization to cDNA which is the same sense as mRNA). It is also desirable to linearly amplify second strand cDNA fragments. The generation of fragmented amplified cDNA comprising 3'-hydroxyl groups is described herein. Tailing of the fragmented amplified cDNA with terminal transferase can be achieved by methods described in the above references and well known in the art. It is desirable to limit the length of the tail, which can be achieved by controlling the reaction conditions, the amount of the incorporated dNTP or rNTP or the use of a mixture of dNTP in the presence of a terminator such as a ddNTP. Tailing of fragmented cDNA products (produced from a single mRNA or multiplicity of mRNA or total RNA) results in the generation of a whole representative population of fragmented cDNA (libraries) with a common consensus 3'-end sequence.

These products may be amplified using a first chimeric primer comprising a 3'-DNA portion that is hybridizable to the 3' tail sequence of the tailed fragmented cDNA and a 5'-RNA sequence which is not hybridizable to the fragmented cDNA products. DNA polymerase comprising both DNA-dependent RNA-dependent DNA polymerase activities may be used to extend the 3' ends of the fragmented and tailed cDNA along the hybridized chimeric primer and the 3'-end of the hybridized primer along the hybridized fragmented and tailed cDNA, to generate double stranded DNA products with an RNA/DNA heteroduplex at one end. The DNA-dependent DNA polymerase and RNA-dependent DNA polymerase may be activities of the same enzyme or of two different enzymes. Extension of the tailed fragmented polynucleotide along the first chimeric primer requires that the 3' end of the fragmented and tailed polynucleotide be unblocked. Therefore, it is desirable to tail the fragmented polynucleotide with nucleotides that do not serve as terminators. This requirement dictates the type of tailing reaction mixtures and conditions used for the tailing reaction. Amplification of this product may proceed by the addition of a second amplification chimeric primer that contains a sequence homologous to the sequence of the RNA portion of the first chimeric primer, RNase H, and a DNA polymerase with strand displacement activity, as previously described (U.S. Pat. Nos. 6,251,239 and 6,692,918). Extension of the first primer along the fragmented polynucleotide is not essential to the process, and thus a 3'-blocked first chimeric primer may also be useful for this process.

The multiplicity of copies of the fragmented cDNA as described above is useful for further analysis and characterization by any of the methods described below. The single stranded amplification products can be labeled by incorporation of labeled nucleotides, tailing of the single stranded amplification products with labeled nucleotides using terminal transferase, and incorporation of nucleotides which can be labeled post-DNA synthesis, such as, for example, aminoallyl-dUTP or various non-enzymatic methods for labeling of nucleic acids (for example, ULS labeling, Kreatech).

Applications Using the Labeling and/or Fragmentation and/or Immobilization Methods of the Invention The methods and compositions of the invention can be used for a variety of purposes. For purposes of illustration, methods of producing a hybridization probe, characterizing and/or quantitating nucleic acid, detecting a mutation, preparing a subtractive hybridization probe, detection (using the hybridization probe), and determining a gene expression profile, using the labeled and/or fragmented nucleic acids generated by the methods of the invention, are described.

Immobilized polynucleotides, for example on a microarray, prepared according to any of the methods of the invention, are also useful for methods of analyzing and characterizing nucleic acids, including methods of hybridizing nucleic acids, methods of characterizing and/or quantitating nucleic acids, methods of detecting a mutation in a nucleic acids, and methods of determining a gene expression profile, as described below, and these applications likewise apply to immobilized polynucleotides.

Method of Producing a Hybridization Probe

Labeled polynucleotide fragments obtained by the methods of the invention are useful as hybridization probes. Accordingly, in one aspect, the invention provides methods for nucleic acid hybridization, comprising using a labeled polynucleotide fragment as a hybridization probe, wherein the labeled polynucleotide fragment is produced using a method as described herein. In one embodiment, the invention provides a method for generating hybridization probes, comprising generating labeled polynucleotides using any of the methods described herein, and using the labeled polynucleotides as a hybridization probe. In another embodiment, the invention provides methods for generating a hybridization probe, comprising generating labeled polynucleotide fragments using any of the methods described herein, and using the labeled polynucleotide fragments as a hybridization probe. The labeled polynucleotide fragments can be produced from any template known in the art, including RNA, DNA, genomic DNA (including global genomic DNA amplification), and libraries (including cDNA, genomic or subtractive hybridization library). The invention also provides methods of hybridizing using the hybridization probes described herein.

Characterization of Nucleic Acids

The labeled and/or fragmented nucleic acids obtained by the methods of the invention are amenable to further characterization.

The fragmented nucleic acids, or labeled fragments thereof (i.e., products of any of the methods described herein), can be analyzed using, for example, probe hybridization techniques known in the art, such as Southern and Northern blotting, and hybridizing to probe arrays. They can also be analyzed by electrophoresis-based methods, such as differential display and size characterization, which are known in the art.

In one embodiment, the methods of the invention are utilized to analyze polynucleotide fragments, wherein the polynucleotide fragments are generated using a method as described herein. In one embodiment, the invention provides a method for analyzing polynucleotides, comprising generating polynucleotide fragments, e.g., labeled polynucleotide fragments, according to a method as described herein, and contacting the polynucleotide fragments with a probe. The polynucleotide fragments can be produced from any template known in the art, including RNA, DNA, genomic DNA (including global genomic DNA amplification), or amplified products thereof, and libraries (including cDNA, genomic or subtractive hybridization library).

In one embodiment, the methods of the invention are utilized to generate fragmented polynucleotides which are analyzed (for example, detection and/or quantification) by contacting them with, for example, microarrays (of any suitable substrate, which includes glass, chips, plastic), beads, or particles, that comprise suitable probes such as cDNA and/or oligonucleotide probes. Thus, the invention provides methods to characterize (for example, detect and/or quantify and/or identify) a fragmented and labeled polynucleotide by analyzing the labeled products, for example, by hybridization of the labeled products to, for example, probes immobilized at, for example, specific locations on a solid or semi-solid substrate, probes immobilized on defined particles (including beads, such as Bead Array, Illumina), or probes immobilized on blots (such as a membrane), for example arrays, or arrays of arrays. Immobilized probes include immobilized probes generated by the methods described herein, and also include at least the following: cDNA and synthetic oligonucleotides, which can be synthesized directly on the substrate.

Other methods of analyzing labeled products are known in the art, such as, for example, by contacting them with a solution comprising probes, followed by extraction of complexes comprising the labeled products and probes from solution. The identity of the probes provides characterization of the sequence identity of the products, and thus by extrapolation can also provide characterization of the identity of a template from which the products were prepared (for example, the identity of an RNA in a solution). For example, hybridization of the labeled products is detectable, and the amount of specific labels that are detected is proportional to the amount of the labeled products prepared from a specific RNA sequence of interest. This measurement is useful for, for example, measuring the relative amounts of the various RNA species in a sample, which are related to the relative levels of gene expression, as described herein. The amount of labeled products (as indicated by, for example, detectable signal associated with the label) hybridized at defined locations on an array can be indicative of the detection and/or quantification of the corresponding template RNA species in the sample.

Methods of characterization include sequencing by hybridization (see, e.g., Dramanac, U.S. Pat. No. 6,270,961) and global genomic hybridization (also termed comparative genome hybridization) (see, e.g., Pinkel, U.S. Pat. No. 6,159,685).

In another aspect, the invention provides a method of quantitating fragmented polynucleotides comprising use of an oligonucleotide (probe) of defined sequence (which may be immobilized, for example, on a microarray).

Mutation Detection Utilizing the Methods of the Invention

The fragmented polynucleotides generated according to the methods of the invention are also suitable for analysis for the detection of any alteration in the template nucleic acid sequence (from which the fragmented polynucleotides are synthesized), as compared to a reference nucleic acid sequence which is identical to the template nucleic acid sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants. Sequence alterations (interchangeably called "mutations") include deletion, substitution, insertion and/or transversion of one or more nucleotide.

Accordingly, the invention provides methods of detecting presence or absence of a mutation in a template, comprising analyzing a polynucleotide fragment generated using a method as described herein, whereby presence or absence of a mutation is detected. In one embodiment, the method comprises: (a) generating a polynucleotide fragment, e.g., a labeled polynucleotide fragment, by any of the methods described herein; and (b) analyzing the polynucleotide fragment whereby presence or absence of a mutation is detected. In some embodiments, the polynucleotide fragment is compared to a labeled reference template, or fragments thereof. Analyzing the polynucleotide fragment, whereby presence or absence of a mutation is detected, can be performed by any method known in the art. In some embodiments, probes for detecting mutations are provided as a microarray.

Any alteration in the test nucleic acid sequence, such as base substitution, insertions or deletion, could be detected using this method. The method is expected to be useful for detection of specific single base polymorphism, SNP, and the discovery of new SNPs.

Other art recognized methods of analysis for the detection of any alteration in the template nucleic acid sequence, as compared to a reference nucleic acid sequence, are suitable for use in the methods of the present invention. For example, essentially any hybridization-based method of detection of mutations is suitable for use with the fragmented polynucleotides produced by the methods of the invention.

Determination of Gene Expression Profile

The fragmented polynucleotides, e.g., labeled polynucleotide fragments, produced by the methods of the invention are particularly suitable for use in determining the levels of expression of one or more genes in a sample. As described above, fragmented polynucleotides can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of RNA sequences of interest present in a sample, as determined by quantifying products (for example amplification products) of the sequences, provides for determination of the gene expression profile of the sample source.

Accordingly, the invention provides methods of determining gene expression profile in a sample, said method comprising: amplifying single stranded (or double stranded) product from at least one RNA sequence of interest in the sample; generating an abasic site in the amplified product; fragmenting the polynucleotide comprising the abasic site according to the methods described herein; and determining amount of fragmented polynucleotide produced from each RNA sequence of interest, wherein each said amount is indicative of amount of each RNA sequence of interest in the sample, whereby the expression profile in the sample is determined.

Accordingly, the invention provides of determining gene expression profile in a sample, comprising determining the amount of a polynucleotide fragment produced from a polynucleotide template as described herein, wherein the amount of a fragment is indicative of the amount of the polynucleotide template in the sample from which the template was derived, whereby a gene expression profile in the sample is determined. In one embodiment, the method comprises: (a) generating a polynucleotide fragment, e.g., a labeled polynucleotide fragment, from at least one polynucleotide template in the sample using any of the methods described herein; and (b) determining amount of polynucleotide fragment produced from of each polynucleotide template, wherein each said amount is indicative of amount of each polynucleotide template in the sample, whereby the gene expression profile in the sample is determined.

It is understood that amount of fragmented polynucleotide produced (and thus the amount of product) may be determined using quantitative and/or qualitative methods. Determining amount of fragmented polynucleotides includes determining whether fragmented polynucleotides are present or absent. Thus, an expression profile can include information about presence or absence of one or more RNA sequence of interest. "Absent" or "absence" of product, and "lack of detection of product" as used herein includes insignificant, or de minimus levels.

The methods of expression profiling are useful in a wide variety of molecular diagnostics, and especially in the study of gene expression in essentially any cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Methods of Preparing a Subtractive Hybridization Probe

Fragmented polynucleotides, e.g., labeled fragmented polynucleotides produced by methods of the invention are particularly suitable for use in preparation of subtractive hybridization probes. For example, two nucleic acid populations, one sense and one antisense, can be allowed to mix together with one population present in molar excess ("driver"). Sequence present in both populations will form hybrids, while sequences present in only one population remain single-stranded. Thereafter, various well-known techniques are used to separate the unhybridized molecules representing differentially expressed sequences. See, e.g., Hamson et al., U.S. Pat. No. 5,589,339; Van Gelder, U.S. Pat. No. 6,291,170.

Comparative Hybridization

In another aspect, the invention provides methods for comparative hybridization (such as comparative genomic hybridization), said method comprising: (a) preparing a first population of polynucleotide fragments from a first template polynucleotide sample using any of the methods described herein; (b) comparing hybridization of the first population to at least one probe with hybridization of a second population of labeled polynucleotides or fragments thereof. In some embodiments, the at least one probe is a chromosomal spread. In still other embodiments, the at least one probe is provided as a microarray. In some embodiments, the first and second population comprise detectably different labels. In other embodiments, a second population of polynucleotide fragments is prepared from a second polynucleotide sample using any of the methods described herein. In some embodiments, comparing comprises determining amount of the products, whereby the amount of the first and second polynucleotide templates is quantified.

In some embodiments, comparative hybridization comprises preparing a first population of labeled polynucleotide fragments according to any of the methods described herein, wherein the template from which the first population is synthesized is genomic DNA. A second population of labeled polynucleotides (to which the first population is desired to be compared) is prepared from a second genomic DNA template. The first and second populations are labeled with different labels. The hybridized first and second populations are mixed, and hybridized to an array or chromosomal spread. The different labels are detected and compared.

The following Examples are provided to illustrate, but not limit, the invention.

EXAMPLES

Example 1

Removal of Blocked 3' Termini and Progressive Degradation of Single Stranded DNA with Processive 3' to 5' Exonuclease Amplified single stranded cDNA comprising dUTP was prepared by isothermal RNA amplification using the Ovation Biotin System (NuGEN Technologies) according to the manufacturer's instruction. Amplified cDNA products generated by amplification of a few total RNA samples (Universal Human RNA, Stratagene, 20 ng each) were purified and pooled. The pooled purified cDNA was used throughout the examples below.

Figure 2:
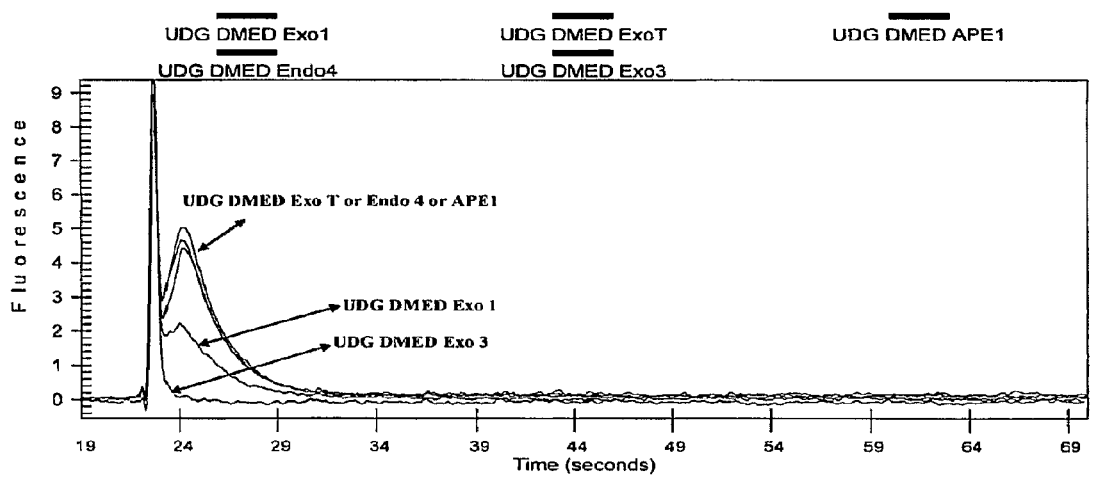
FIG. 2 shows data from an experiment comparing the ability of various 3' exonucleases to unblock blocked 3' ends of polynucleotide fragments, as described in Example 1.

Pooled cDNA (5 ug) was mixed with UNG (USB, 4 units) in reaction buffer containing 32 mM DMED, and incubated at 370 C for 30 minutes. As shown previously (U.S. Application No. 2004/0005614), treatment with UNG results in the removal of the base portion of dU residues and formation of abasic sites. DMED cleaves the backbone to generate fragmented DNA with 3'-modified termini. The blocked 3'-end can be removed by a 3' to 5'-exonucleases to generate a 3' hydroxyl group. Insofar as the aim of this procedure is to generate fragmented DNA with 3'-OH termini, it is desirable to use a non processive exonuclease so as to assure limited hydrolysis of the fragmented DNA. The nuclease activities of exonuclease 1 (Exo1), exonuclease 3 (Exo3), exonuclease T (ExoT), endonuclease D (Endo4), and APE1 (NEB) were tested. The UNG and DMED treated amplified cDNA was purified (DyeEx, Qiagen) and the purified product was incubated with the various enzymes in the respective reaction buffers (as per the manufacturer instructions). Following 30 min. incubation at 370 C, the products were purified and the size of the treated products was analyzed electrophoretically (BioAnalyzer, Agilent). The more processive the 3' to 5' exonuclease activity of a given enzyme, the greater the expected result in reduced size and reduction in quantity of the fragmented single stranded cDNA population. As shown in FIG. 2, processive exonuclease activity of Exo1 and Exo3 resulted in reduced product recovery and reduced size of the recovered fragmented cDNA, as compared to that of the UNG and DMED fragmented cDNA substrate. The non processive 3'-exonuclease activity of endonuclease 4, exonuclease T, and APE1, on the other hand, resulted in product distribution size similar to the input fragmented cDNA (UNG and DMED treated amplified cDNA). Further evidence for the non processive 3'-deblocking activity of these enzymes was obtained by the demonstration of the ability to end label the fragmented cDNA treated with these enzymes by template-independent extension of the 3-OH termini of the cDNA by terminal transferase, as described in Example 2 below.

Figure 3:
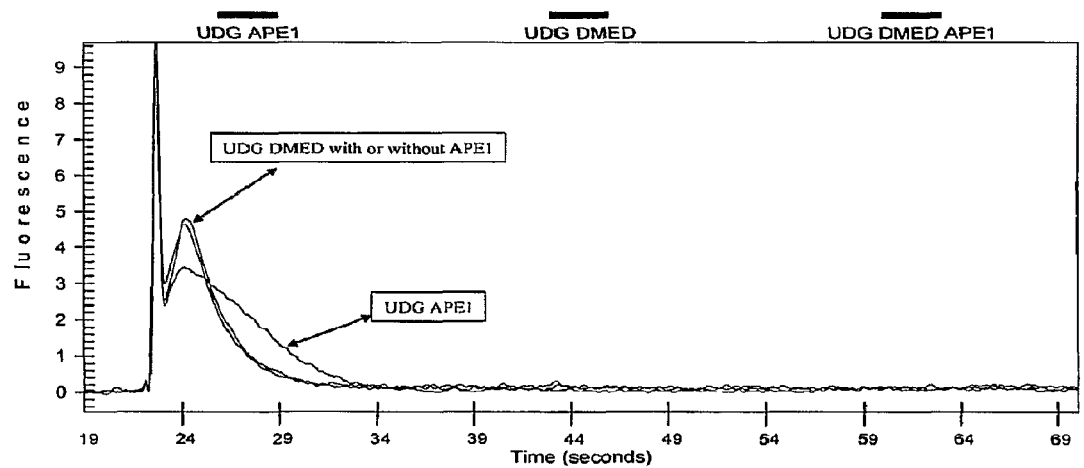
FIG. 3 shows data from an experiment demonstrating the ability of terminal deoxynucleotidyl transferase (TdT) to label 3' hydroxyl groups of polynucleotide fragments which after blocked 3' ends were unblocked by treatment with apurinic/apyrimidinic exonuclease 1 (APE 1), as described in Example 2.

APE1 is a multifunctional repair enzyme comprising an endonuclease activity for the excision of abasic sites and subsequent fragmentation of the DNA template to generate fragments with 3-OH termini, on the one hand, and a 3' to 5' exonuclease activity for the removal of the blocked 3'-end of damaged DNA template. As shown in FIG. 3, treatment of amplified cDNA comprising abasic sites (amplified cDNA treated with the specific glycosylase, UNG), with APE1 (40 units) led to partial fragmentation of the cDNA template, as compared to the size distribution of DMED fragmented amplified cDNA comprising abasic sites. The relative inefficiency of APE1 endonuclease activity for full fragmentation of the amplified cDNA template comprising abasic site resulted in the requirement of a large amount of the enzyme. Full fragmentation of the template DNA was achieved in reactions carried out with 500 to 1000 units of APE1 (data not shown). The 3' to 5' exonuclease activity of the enzyme is very efficient, and the non processive exonuclease activity enables the de-blocking of the 3'-end of template cDNA fragmented by the combined treatment with UNG (to generate abasic sites) and DMED (to fragment the DNA backbone while leaving an aldehyde group at the 3' termini). Use of the exonuclease activity of the enzyme for the generation of fragments with 3'-OH termini was validated by the ability to end label the fragmented and de-blocked template by terminal transferase template-independent extension with labeled nucleotide (biotin end labeling) as described in Example 2 below.

Example 2

Generation of Fragmented cDNA with 3'-Termini which are Suitable for Labeling by Template Independent Extension Using Terminal Deoxynucleotidyl Transferase (TdT) and Labeled Nucleotide Pooled amplified cDNA comprising dU residues was prepared as described in Example 1. Treatment of the pooled cDNA with UNG and DMED, as described in Example 1, was used to generate fragmented cDNA with blocked 3'-OH termini. A cDNA fragment with a blocked 3' terminus can be labeled with an aldehyde reactive conjugate of a desired label to yield fragmented and labeled cDNA target suitable for microarray based analysis (U.S. Application No. 2004/0005614; Dafform et al. (2004) "BioTechniques 37:854-857; Kurn et al. (2005) Clinical Chemistry 51:1973-1981). However, extension of the fragmentation process to polymerase extension based end labeling (e.g., terminal transferase template independent labeling) requires deblocking of the 3'-termini. As discussed in Example 1, various non processive 3'-to-5' exonucleases were tested for the ability to deblock the blocked 3' termini of such fragments. The validation of the ability to generate suitable substrates for end labeling was obtained by end labeling of the pooled fragmented and nuclease treated targets for end labeling with TdT (terminal deoxynucleotidyl transferase) and biotin labeled ddUTP. End labeling of the targets was assessed by hybridization of the targets to high density Human Focus GeneChip arrays (Afymetrix). Various array analysis parameters obtained with the various targets are shown in Table 1.

End labeling of the various fragmented cDNA products with TdT was carried out under the following conditions: The reactions were carried out in 1×NEB buffer #4 (50 mM potassium acetate, 20 mM Tris-Acetate, 10 mM magnesium acetate, 1 mM DTT, pH 7.9), 0.25 mM CoCl2, in the presence of 0.5 nmol Biotin 2',3'-dideoxy-UTP (Roche), and 40 U TdT, in a total volume of 50 µl. The TdT reactions were carried out at 37° C. for 60 min. followed by TdT inactivation (70° C. for 15 min). The reaction products were added to a GeneChip hybridization mixture. Hybridization, wash, signal generation and array scanning were carried out as per the manufacturer instructions.

TABLE 1

Array Analysis Parameters

| Array | Targets | Raw Q | Scaling Factor | Background | % Present | (3'/5') GAPDH |
|---|---|---|---|---|---|---|
| 1 | UNG, DMED, TdT, ddUTP | 0.88 | 276.1 | 30.4 | 4.3 | 1.40 |
| 2 | UNG, APE1(30U), TdT, ddUTP | 0.93 | 44.1 | 32.3 | 32.3 | 1.84 |

TABLE 1-continued

Array Analysis Parameters

| Array | Targets | Raw Q | Scaling Factor | Background | % Present | (3'/5') GAPDH |
|---|---|---|---|---|---|---|
| 3 | UNG, DMED, DyeEx ExoT, TdT, ddUTP | 0.99 | 60.6 | 31.6 | 25.5 | 2.20 |
| 4 | UNG, DMED, DyeEx Endo4, TdT, ddUTP | 1.19 | 24.6 | 34.8 | 38.3 | 2.13 |
| 5 | UNG, DMED, DyeEx APE10U, TdT, ddUTP | 1.04 | 16.7 | 28.2 | 47.2 | 2.25 |
| 6 | UNG, DMED, DyeEx APE50U. TdT, ddUTP | 1.16 | 17.1 | 33.9 | 45.4 | 1.90 |
| 7 | UNG, DMED, APE10U, TdT, ddUTP | 0.92 | 30.9 | 26.3 | 41 | 2.25 |
| 8 | UNG, DMED 100 mM, pH 7.4, Mg 0.4 mM, APE10U, TdT, ddUTP | 1.06 | 8.3 | 31.9 | 56.8 | 1.54 |
| 9 | UNG, DMED 100 mM, pH 7.4, Mg 2 mM, APE10U, TdT, ddUTP | 1.01 | 6.5 | 31.1 | 60.4 | 1.47 |
| 10 | UNG, DMED 34 mM, pH 7.4, Mg 4 mM, APE10U, TdT, ddUTP | 1.07 | 4.0 | 31.7 | 64.0 | 1.50 |

Results

Array 1: The target was generated by Biotin 3'-end labeling of fragmented targets which were not further treated with exonuclease to unblock the 3' termini. The high Scaling Factor and low percent of genes called Present (% Present), represent poor labeling and are consistent with the inability to extend the 3'-blocked target for end labeling.

Removal of the abasic site generated by UNG by APE1, which cleaves the phosphodiester bond 5' to the abasic site sugar, generating a nick with 5' sugar phosphate (dRP) and 3' hydroxyl group at the 3'-end, enabling the biotin labeling of the fragmented cDNA targets by TdT. The endonuclease activity results in lower Scaling Factor and higher % Present results as compared to Array 1. However, this array performance is not optimal as the cDNA fragment sizes are larger than DMED cuts (as seen in FIG. 3). The results indicate that the endonuclease activity of APE1 is not sufficient to efficiently fragment the cDNA comprising abasic sites to the proper size required for efficient hybridization to the high density GeneChip arrays (Affymetrix).

Arrays 3 and 4: Purified cDNA comprising dU residues was fragmented by the action of UNG and DMED and further treated with exo T or the exonuclease activity of Endo 4, respectively. The results indicate efficient exonuclease activity of these nonprocessive exonucleases so as to unblock the 3'-termini and enable end-labeling by TdT and ddUTP.

Arrays 5 and 6: Similar labeling efficiency was enabled by unblocking of the DMED fragmented cDNA by the exonuclease activity of APE1 when present at either 10 or 50 units per reaction.

Array 7: The reaction condition was the same as for the target hybridized to array 5, except that UNG generation of abasic sites, DMED fragmentation of the cDNA at the abasic sites and unblocking of the 3'-end of the fragmented cDNA by APE1 were carried out in a single reaction mixture (30 mi. at 37° C.). The array results obtained with these reaction conditions provided a comparison for arrays 8, 9, and 10 as generation of abasic sites, fragmentation, and unblocking of 3' end occurred in a single reaction.

Arrays 8, 9 and 10: Reaction conditions for the generation of fragmented cDNA with 3'-OH termini were assessed. The best performance (as per the ability to efficiently biotin-end-label the products by TdT for improved array results) was observed with conditions for target hybridized to array 10. As described for targets hybridized to arrays 8 and 9, UNG, DMED and APE1 were reacted in a single reaction mixture. The general superior performance for this group of arrays is attributed to the reaction buffer condition that favored 3'- to 5'-exonuclease activity of APE1. The buffer condition changes included lower $Mg^{2+}$ concentration, no $Na^+$, and the reaction pH at 7.4. (Chou et al. (2003) *J. Biol. Chem.* 278(20): 18289-96.

All publications, patents, and patent applications cited herein are hereby incorporated by reference in their entireties for all purposes and to the same extent as if each individual publication, patent, or patent application were specifically and individually indicated to be so incorporated by reference.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

We claim:

1. A method comprising:
   (a) cleaving a base portion of at least one non-canonical nucleotide from a polynucleotide, wherein the polynucleotide comprises at least one non-canonical nucleotide, wherein the cleaving comprises use of uracil N-glycosylase (UNG), thereby generating an abasic site in the polynucleotide;
   (b) fragmenting a phosphodiester backbone of the polynucleotide at the abasic site using N,N'-dimethylethylenediamine (DMED), thereby forming a polynucleotide fragment with a blocked 3' end;
   (c) unblocking the blocked 3' end of the polynucleotide fragment with an enzyme comprising a nonprocessive 3' to 5' exonuclease activity, thereby generating a polynucleotide fragment with a 3' hydroxyl; and
   (d) extending the polynucleotide fragment with the 3' hydroxyl from the 3' hydroxyl using terminal deoxynucleotidyl transferase (TdT).

2. The method according to claim 1, wherein the enzyme comprising the nonprocessive 3' to 5' exonuclease activity does not comprise an endonuclease activity.

3. The method according to claim 1, wherein the enzyme comprising the nonprocessive 3' to 5' exonuclease activity also comprises an endonuclease activity, and wherein the endonuclease activity is minimized or absent.

4. The method according to claim 1, wherein the enzyme comprising the nonprocessive 3' to 5' exonuclease activity is selected from the group consisting of endonuclease 4, exonuclease T, and apurinic/apyrimidinic endonuclease (APE 1).

5. The method according to claim 1, wherein the extending further comprises a labeled nucleotide, whereby a polynucleotide fragment labeled at a 3' end is generated.

6. The method according to claim 5, wherein the labeled nucleotide is selected from the group consisting of a labeled nucleotide triphosphate (NTP), a labeled deoxynucleotide triphosphate (dNTP), and a labeled dideoxynucleotide triphosphate (ddNTP).

7. The method according to claim 5, wherein the labeled nucleotide is a biotinylated nucleotide.

8. The method according to claim 5, wherein the labeled nucleotide comprises a fluorophore.

9. The method according to claim 5, wherein a mixture of labeled and unlabeled nucleotides is used for labeling the polynucleotide fragment.

10. The method according to claim 1, wherein the non-canonical nucleotide is dUTP.

11. The method according to claim 1, wherein the polynucleotide comprising at least one non-canonical nucleotide is synthesized in the presence of two or more different non-canonical nucleotides, whereby a polynucleotide comprising two or more different non-canonical nucleotides is synthesized.

12. The method according to claim 1, wherein the polynucleotide comprising a non-canonical nucleotide is synthesized in the presence of all four canonical nucleotides and a non-canonical nucleotide.

13. The method according to claim 5, further comprising analyzing the polynucleotide fragment labeled at the 3' end.

14. The method according to claim 13, wherein the analyzing the polynucleotide fragment labeled at the 3' end comprises determining an amount of polynucleotide, whereby an amount of the polynucleotide template present in a sample is quantified.

15. The method according to claim 13, wherein the analyzing the polynucleotide fragment labeled at the 3' end comprises contacting the polynucleotide fragment labeled at the 3' end with at least one probe.

16. The method according to claim 15, wherein the at least one probe is provided as a microarray.

17. The method according to claim 5, further comprising determining a gene expression profile in a sample, comprising determining an amount of the polynucleotide fragment labeled at the 3' end wherein the amount is indicative of an amount of a polynucleotide template in the sample from which the polynucleotide fragment labeled at the 3' end was generated, whereby a gene expression profile is determined.

18. The method according to claim 17, wherein the polynucleotide template is RNA or mRNA.

19. The method according to claim 17, wherein the amounts of a plurality of polynucleotide fragments derived from a plurality of polynucleotide templates in the sample are determined.

20. The method according to claim 5, further comprising hybridizing a first population of polynucleotide fragments labeled at the 3' end to at least one probe.

21. The method according to claim 20, further comprising comparing hybridization of the first population of polynucleotide fragments labeled at the 3' end to at least one probe with hybridization of a second population of polynucleotide fragments labeled at the 3' end to the at least one probe.

22. The method according to claim 5, further comprising detecting a presence or absence of a mutation in a template, comprising analyzing the polynucleotide fragment labeled at the 3' end, whereby the presence or absence of the mutation is detected, wherein the analyzing comprises comparison of the polynucleotide fragment labeled at the 3' end to a polynucleotide prepared from a reference polynucleotide.

23. The method according to claim 22, wherein the mutation is selected from the group consisting of a base substitution, a base insertion, a base deletion, and a single nucleotide polymorphism.

24. The method according to claim 1, wherein the polynucleotide comprising the at least one non-canonical nucleotide is synthesized from a polynucleotide template comprising DNA or RNA.

25. The method according to claim 24, wherein the polynucleotide template is selected from the group consisting of mRNA, cDNA, and genomic DNA.

26. The method according to claim 1, wherein the polynucleotide comprising the at least one non-canonical nucleotide is single stranded or double stranded.

27. The method according to claim 1, wherein the polynucleotide comprising the at least one non-canonical nucleotide is synthesized by an amplification method selected from the group consisting of polymerase chain reaction (PCR), strand displacement amplification (SDA), multiple displacement amplification (MDA), rolling circle amplification (RCA), single primer isothermal amplification (SPIA), and Ribo-SPIA.

28. The method according to claim 1, wherein the polynucleotide comprising the at least one non-canonical nucleotide is synthesized by a method selected from the group consisting of reverse transcription, primer extension, limited primer extension, replication, and nick translation.

29. A method according to claim 1 wherein (a) and (b) are performed simultaneously and performed in the same reaction mixture.

* * * * *